(12) United States Patent
Ueki et al.

(10) Patent No.: US 9,818,182 B2
(45) Date of Patent: Nov. 14, 2017

(54) X-RAY CT DEVICE

(71) Applicant: HITACHI, LTD., Tokyo (JP)

(72) Inventors: Hironori Ueki, Tokyo (JP); Yushi Tsubota, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/409,100

(22) PCT Filed: Jun. 6, 2013

(86) PCT No.: PCT/JP2013/065639
§ 371 (c)(1),
(2) Date: Dec. 18, 2014

(87) PCT Pub. No.: WO2013/191001
PCT Pub. Date: Dec. 27, 2013

(65) Prior Publication Data
US 2015/0324973 A1  Nov. 12, 2015

(30) Foreign Application Priority Data

Jun. 20, 2012  (JP) ................................. 2012-138283

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/504* (2013.01); *A61B 6/5205* (2013.01); *G01T 1/24* (2013.01); *G01T 1/2985* (2013.01); *G06T 11/005* (2013.01); *H04N 5/32* (2013.01); *H04N 5/378* (2013.01); *A61B 6/4021* (2013.01); *A61B 6/465* (2013.01); *A61B 6/582* (2013.01);
(Continued)

(58) Field of Classification Search
None
See application file for complete search history.

(56) References Cited

U.S. PATENT DOCUMENTS 4,504,962 A * 3/1985 Moore .................... A61B 6/032
378/10
4,897,788 A * 1/1990 King ...................... A61B 6/583
378/12
(Continued)

FOREIGN PATENT DOCUMENTS

JP  2002-022678 A  1/2002
JP  2004-325183 A  11/2004
(Continued)

OTHER PUBLICATIONS

International Search Report from International Application No. PCT/JP13/065639 dated Jul. 30, 2013.

*Primary Examiner* — Avinash Yentrapati
(74) *Attorney, Agent, or Firm* — Brundidge & Stanger, P.C.

(57) ABSTRACT

The present invention prevents aliasing of the X-ray detector from lowering the spatial resolution and enhances the precision of measurement in an X-ray CT device. This has the effect of making it possible to measure finer structures, such as blood vessels, and enhance the diagnostic capability, without having to increase the subject's exposure in, for example, medical CT.

13 Claims, 29 Drawing Sheets

(51) Int. Cl.
*H04N 5/32* (2006.01)
*H04N 5/378* (2011.01)
*A61B 6/03* (2006.01)
*G01T 1/24* (2006.01)
*G01T 1/29* (2006.01)
*G06T 11/00* (2006.01)
*A61B 6/00* (2006.01)

(52) U.S. Cl.
CPC ........... *G06T 2207/10081* (2013.01); *G06T 2207/10116* (2013.01)

(56) References Cited

U.S. PATENT DOCUMENTS

| | | | | |
|---|---|---|---|---|
| 5,510,622 | A * | 4/1996 | Hu | A61B 6/032 250/366 |
| 5,960,056 | A * | 9/1999 | Lai | A61B 6/032 378/15 |
| 6,243,438 | B1 * | 6/2001 | Nahaliel | A61B 6/032 378/19 |
| 6,437,338 | B1 * | 8/2002 | Hoffman | H04N 3/1562 250/208.1 |
| 6,438,198 | B1 * | 8/2002 | Kohler | A61B 6/032 378/15 |
| 6,963,631 | B2 * | 11/2005 | Brunnett | A61B 6/032 250/370.09 |
| 7,327,824 | B2 * | 2/2008 | Gohno | A61B 6/032 250/366 |
| 2003/0002617 | A1 * | 1/2003 | Hsieh | A61B 6/032 378/19 |
| 2003/0016882 | A1 * | 1/2003 | Riley | G01J 3/28 382/275 |
| 2004/0081279 | A1 * | 4/2004 | Brunnett | A61B 6/032 378/98.8 |
| 2005/0053191 | A1 * | 3/2005 | Gohno | A61B 6/032 378/19 |
| 2006/0138333 | A1 * | 6/2006 | Nascetti | H04N 3/1562 250/370.09 |
| 2007/0280409 | A1 * | 12/2007 | Konno | A61B 6/032 378/19 |
| 2008/0095299 | A1 * | 4/2008 | Kohler | G01T 1/1647 378/4 |
| 2008/0118023 | A1 * | 5/2008 | Besson | A61B 6/06 378/8 |
| 2009/0080601 | A1 * | 3/2009 | Tkaczyk | G01T 1/24 378/19 |
| 2009/0148023 | A1 * | 6/2009 | Spahn | A61B 6/4208 382/132 |
| 2009/0257553 | A1 * | 10/2009 | Goto | G06T 11/005 378/19 |
| 2012/0166128 | A1 * | 6/2012 | Ikhlef | A61B 6/583 702/104 |
| 2013/0108009 | A1 * | 5/2013 | Kojima | A61B 6/032 378/7 |
| 2014/0177795 | A1 * | 6/2014 | Spahn | A61B 6/484 378/62 |
| 2014/0341347 | A1 * | 11/2014 | Radicke | G01N 23/04 378/62 |

FOREIGN PATENT DOCUMENTS

| | | |
|---|---|---|
| JP | 2005-349080 A | 12/2005 |
| JP | 2006-503631 A | 2/2006 |
| JP | 2006-314425 A | 11/2006 |
| JP | 2007-529258 A | 10/2007 |
| WO | 2004/037089 A1 | 5/2004 |
| WO | 2011/018729 A1 | 2/2011 |

* cited by examiner (A)

(B)

(C)

(D)

(A)

(B)

(C)

(A)

(B)

(C)

(A)

(B)

(A)

(B)

(A)

(B)

X-RAY CT DEVICE

TECHNICAL FIELD

The present invention pertains to an X-ray CT device and more particularly relates to a technology of improving spatial resolution, thereby improving measurement precision for an object.

BACKGROUND ART

The X-ray CT (Computed Tomography) device is a device that captures X-ray transmission data of the object while rotating a pair (hereinafter, referred to as a scanner) of an X-ray source and an X-ray detector that have been oppositely arranged with the object interposed and computationally reconstructs a tomographic image thereof (hereinafter, referred to as a CT image), and is widely used in the fields of industrial and security inspection devices, medical image diagnostic devices and so forth. In the field of the medical X-ray CT devices, area increasing of an X-ray detector and speeding-up of rotation of the scanner have been recently promoted and it has become possible to measure an image scanning region of a wide range in a short period of time. In addition, in association with improvement in time resolution owing to speeding-up of the rotational speed of the scanner, the measurement precision for moving objects such as the heart and a coronary artery has been remarkably improved. In association with such upgrading of X-ray CT measurement, there is a growing need for improvement in spatial resolution. For example, there is such a need that in a stent that has been inserted into a blood vessel in order to expand the blood vessel that has become constricted, it is desired to take a wait-and-see approach on presence/absence of recurrence of the angiostenosis and tissue characteristics of plaques, and the high spatial resolution for inspecting a fine structure of the object is demanded.

In order to improve the spatial resolution in measurement by the X-ray CT device, in general, miniaturization, that is, downsizing of a detection element of the X-ray detector is needed. However, in a case where the dose of X-rays to be incident upon the X-ray detector is the same, since the number of X-ray photons to be incident upon one detection element is reduced when the detection element is miniaturized, the S/N of a detection signal is reduced. Although it is necessary to increase the X-ray dose in order to improve the S/N, in a case of medical measurement, an increase in X-ray dose leads to an increase in exposure of the object. From the above, the size of the detection element of the X-ray detector is determined by trade-off between the spatial resolution and the exposed dose, and in the medical X-ray CT device, in general, an X-ray element having an X-ray input plane of the size of about 1 [mm] square is used.

As a method of improving the spatial resolution without reducing the size of the detection element of this X-ray detector, there is proposed a method in Patent Literature 1. The method shown in Patent Literature 1 is a system called a Flying Focal Spot (FFS) system. In addition, in Patent Literature 2, there is disclosed a configuration example that in order to promote high resolution and high sensitivity of the medical X-ray CT device, a cycle in one direction of a linear projected image of an X-ray shielding member of an X-ray grid on a detection plane of the X-ray detector is set to an integer multiple that is two or more times a cycle of an array of the detection elements substantially in this one direction.

CITATION LIST

Patent Literature

PTL 1: WO 2011/018729 A1
PTL 2: Japanese Patent Application Laid-Open No. 2002-22678

SUMMARY OF INVENTION

Technical Problem

In order to describe a problem of the present invention, first, the outline of the FFS system will be described by using FIG. 30 to FIG. 32. FIG. 30 is a diagram for describing a relation between an X-ray generation point S and a data sample point R in a general X-ray CT device that does not adopt the FFS system. In addition, FIG. 31 is a diagram for describing a relation between X-ray generation points S1 and S2 and respective data sample points R1 and R2 in an X-ray CT device that has adopted the FFS system. However, in FIG. 30 and FIG. 31, it is assumed that an X-axis is a straight line that passes the axis of rotation of a scanner and is parallel with an X-ray detector 2 with an input plane, and an intersection point between a straight line that connects together the X-ray generation point S and each detection element P that configures the X-ray detector 2 and the x-axis is set as the data sample point R. An X-ray beam that is radiated from the X-ray generation point S and is incident upon the detection element P passes through the object that is present at the data sample point R in the vicinity of the axis of rotation of the scanner and is then measured.

Here, in the X-ray CT device that does not adopt the FFS system (hereinafter, referred to as a general system) shown in FIG. 30, relative positions of the X-ray generation point S and the X-ray detector 2 are always fixed in a plurality of image scanning operations to be performed while rotating the scanner. On the other hand, in the X-ray CT device that is shown in FIG. 31 and has adopted the FFS system, the position of the X-ray generation point is alternately changed to S1, S2, S1, S2, . . . for every image scanning. In addition, the positions of S1 and S2 at that time are set such that the data sample points R1, R2 that are formed relative to the respective X-ray generation points are spaced at equal intervals in the X-axis direction. Therefore, a sampling interval in the X-axis direction between the data sample points R1, R2 obtained in the FFS system is reduced to $\Delta X/2$ that is one-half of an interval $\Delta X$ in the X-axis direction between the data sampling points R obtained in the general system.

(A) and (B) of FIG. 32 are diagrams for describing frequency characteristics in the X-axis direction of data acquired at the data sample points R respectively shown in FIG. 30 and FIG. 31. That is, (A) of FIG. 32 is the frequency characteristic of the general system and (B) of FIG. 32 is the frequency characteristic of the FFS system.

Incidentally, in FIG. 32, it is assumed that fn is a Nyquist frequency ($=1/(2\Delta X)$) relative to the sampling interval $\Delta X$ in the general system. On the other hand, in a case where the FFS system has been adopted, since the sampling interval is reduced to $\Delta X/2$ as mentioned above, the Nyquist frequency thereof amounts to 2fn ($=1/\Delta X$) that is two times. In addition, a frequency characteristic 3200 shown in FIG. 32 is the frequency characteristic of an aperture function of the X-ray detection element P. Frequency information included in the object is measured by being subjected to bandwidth limitation by the frequency characteristic 3200 of the above-mentioned aperture function.

Here, in the general system shown in (A) of FIG. 32, the frequency characteristic 3200 repetitively appears at every frequency that is two times the Nyquist frequency fn by a well-known sampling theorem, and a so-called aliasing region 320 where they overlap becomes comparatively large. The above-mentioned aliasing causes high-frequency information included in the object to be lost and causes a reduction in spatial resolution. On the other hand, in the FFS system shown in (B) of FIG. 32, since the Nyquist frequency amounts to 2fn that is two times that of the general system, the frequency characteristic 3200 repetitively appears at every 4fn. Therefore, an aliasing region 3202 that is formed at that time is greatly reduced in comparison with the aliasing region 3201 of the general system. Thereby, since the loss of the high-frequency information caused by aliasing can be reduced in the FFS system, it becomes possible to improve the spatial resolution without reducing the size of the detection element.

As described above, in the ordinary system shown in FIG. 30, since the position of the X-ray generation point S is always fixed relative to the scanner, the X-ray generation point S that is formed with rotation of the scanner draws a continuous locus. On the other hand, in the FFS system shown in FIG. 31, since the position of the X-ray generation point is switched to S1, S2, S1, S2, . . . at every image scanning timing, the locus of the X-ray generation point that is formed with rotation of the scanner becomes discontinuous. At that time, since such irregularities generate at the sampling positions in a rotation angle direction of the scanner that there are generated a place where the loci of the X-ray generation points overlap at S1 and S2, a place where the locus is broken off halfway and so forth, and there was such a problem that a streak-shaped artifact is liable to generate in the CT image in the FFS system due to this.

In addition, although it is necessary to change the X-ray generation point position at a high speed in the FFS system, such position control is specifically implemented by providing a mechanics that controls the position of an electronic beam to be radiated from a cathode in an X-ray tube to a rotational anode by using an electric field and a magnetic field in the X-ray tube. Although addition of such a mechanics leads to an increase in manufacturing cost of the X-ray tube, on the other hand, the X-ray tube is a component that is to be regularly exchanged as a consumption article. That is, in the X-ray CT device that has adapted the FFS system, there existed such a problem that running cost that is incidental to regular exchange of the X-ray tube is increased.

An object of the present invention is to provide an X-ray CT device that improves the spatial resolution without reducing the S/N of the CT image to be measured and makes high precision measurement of the fine structure of the object possible.

Solution to Problem

In order to attain the above-mentioned object, in the present invention, there is provided an X-ray CT device that generates a CT image of an object, including an X-ray generation unit, an X-ray detection unit that detects an X-ray image irradiated from the X-ray generation unit, a rotation mechanics unit that rotates the X-ray generation unit and the X-ray detection unit around the axis of rotation, a signal read-out unit that reads out a signal detected by the X-ray detection unit at a predetermined image scanning timing, and a signal processing unit that processes a signal that has been output from the signal read-out unit to generate the CT image of the object, wherein the signal read-out unit is configured to add and output signals detected by NX detection pixels that are adjacent in an X direction and/or Nz detection pixels that are adjacent in a z direction (here, NX and Nz are integers of 1 or more and either one of them is 2 or more) in the plurality of detection pixels configured in a matrix on an X-ray input plane of the X-ray detection unit, and perform changing of an addition position of the detection pixel where the addition is performed in synchronization with the image scanning timing.

Advantageous Effects of Invention

According to the present invention, in the X-ray CT device, the spatial resolution can be improved without reducing the S/N of the X-ray CT image to be measured.

DESCRIPTION OF EMBODIMENTS

In the following, an embodiment of the present invention will be described on the basis of the drawings. Although details of novel characteristics of the present invention will become apparent from the following description and the appended drawings, first, the principles of the present invention and further the outline of a representative one of them will be described by using FIG. 33. Incidentally, in the present specification, it is assumed that an X direction is a direction that is vertical to the axis of rotation around which an X-ray generation unit and an X-ray detection unit rotate, of many detection pixels detection pixels that are configured in a matrix on an X-ray input plane of the X-ray detection unit that configures the X-ray CT device, and z direction is a direction that is parallel with the axis of rotation of the detection pixel.

Figure 30:
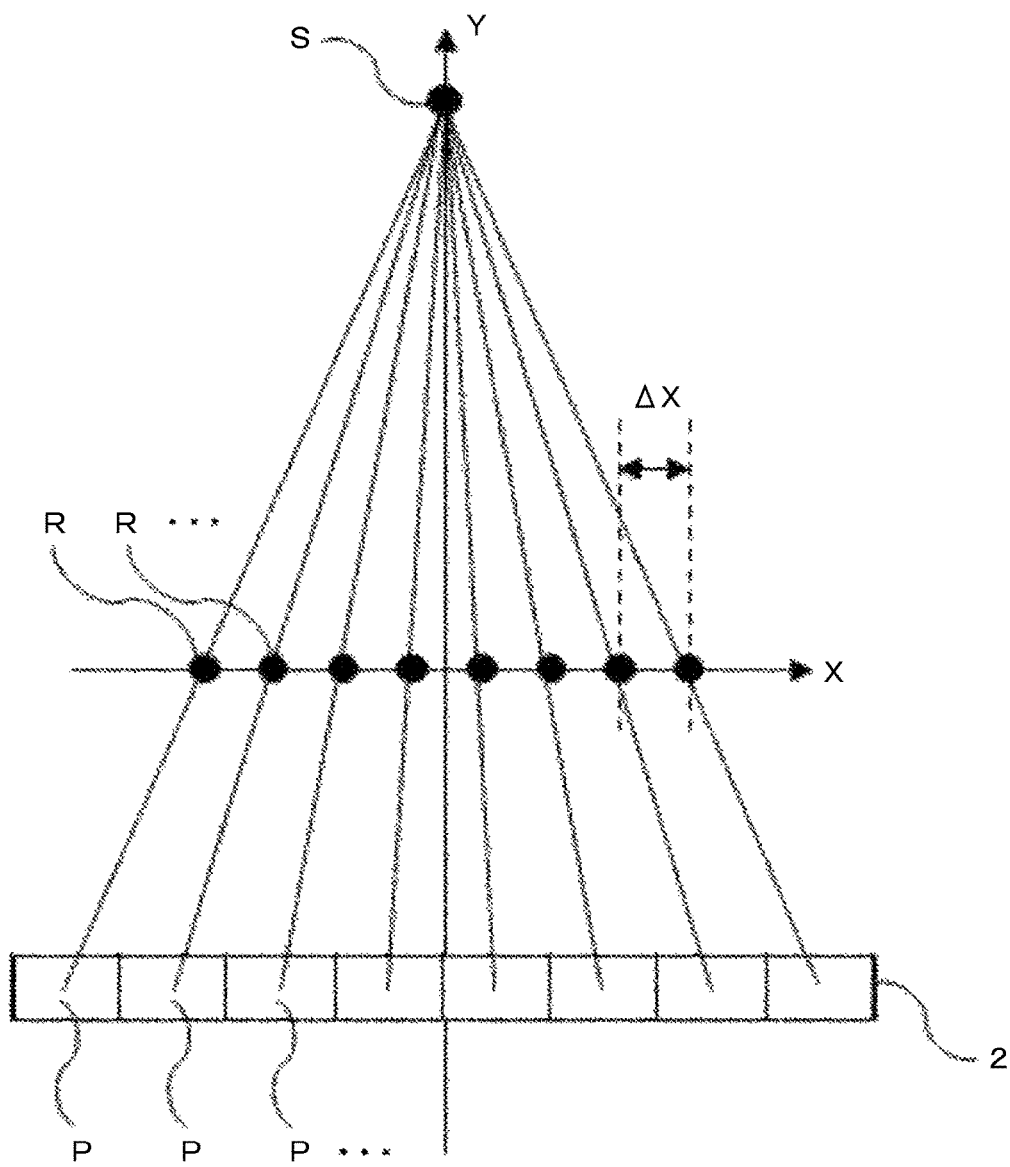
FIG. 30 is a diagram for describing a relation between the X-ray generation point S and the data sample point R in the general X-ray CT device that does not adopt the FFS system.
Figure 31:
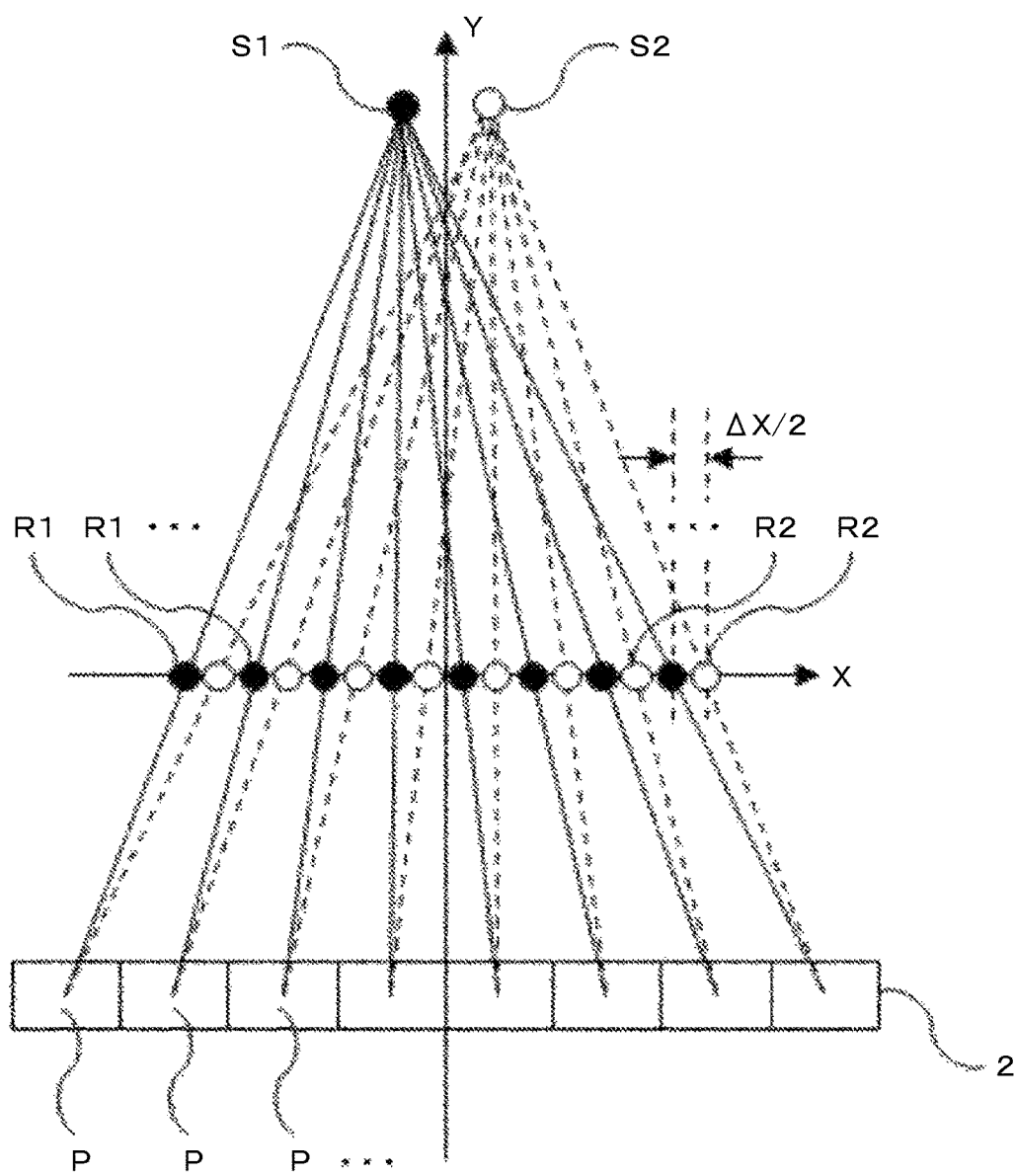
FIG. 31 is a diagram for describing a relation between the X-ray generation points S1 and S2 and respective data sample points R1 and R2 in the X-ray CT device that has adopted the FFS system.
Figure 32:
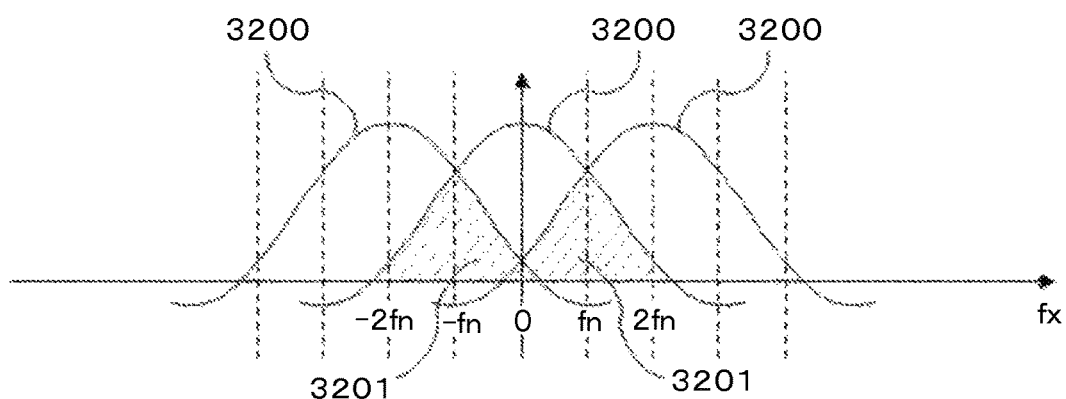
FIG. 32 is diagrams for describing the frequency characteristics in the X-axis direction of the data acquired at the data sample point R shown in FIG. 30 and FIG. 31.
Figure 32:
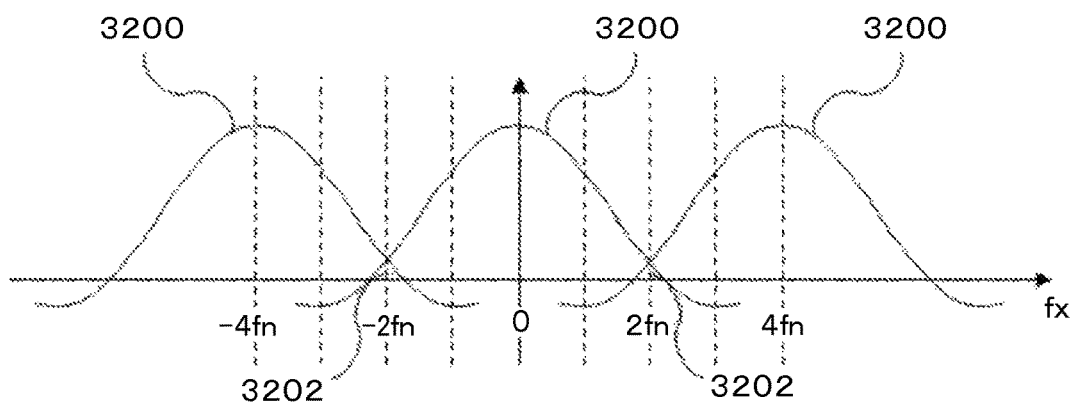
Figure 33:
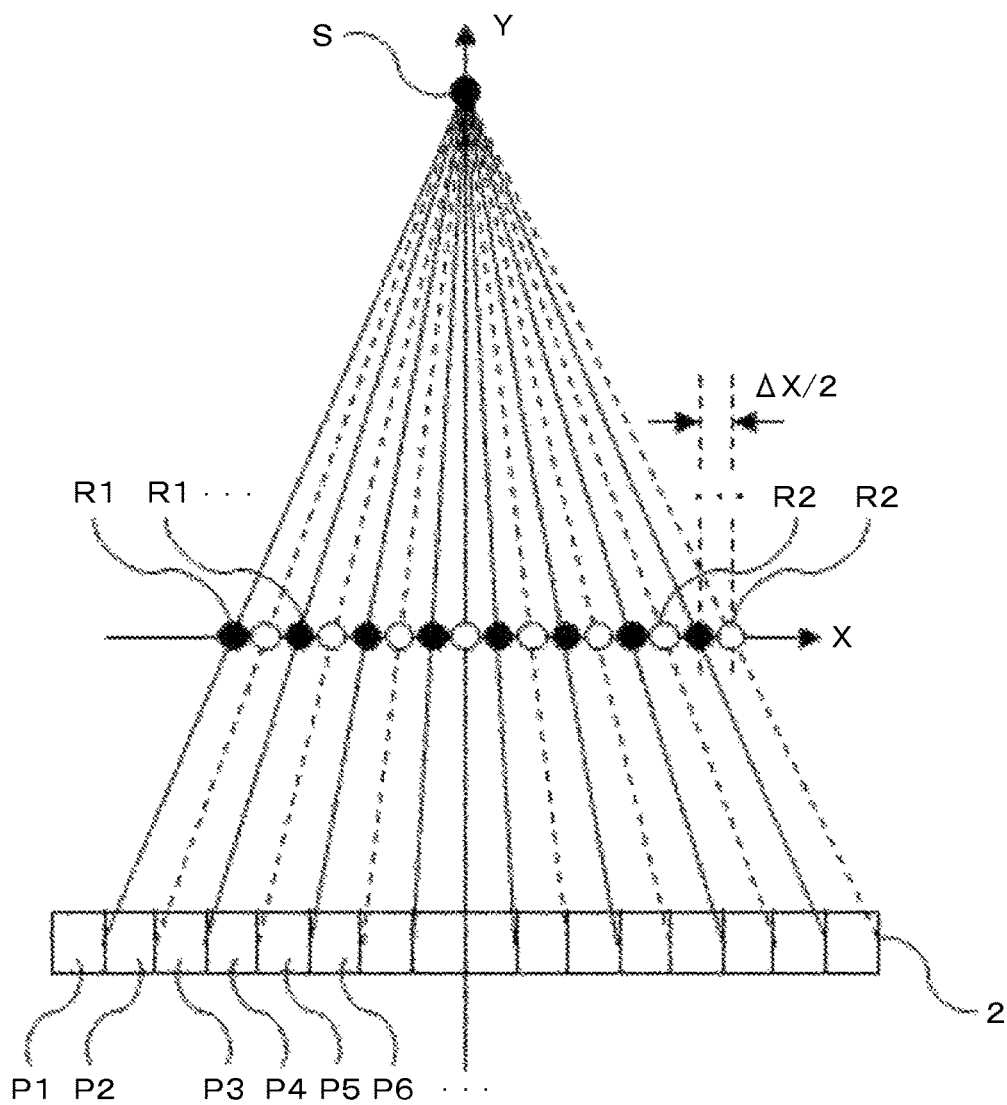
FIG. 33 is a diagram for describing a relation between the X-ray generation point S and the data sample points R1 and R2 in one configuration of the X-ray CT device of the present invention.

FIG. 33 is a diagram for describing a relation between the X-ray generation point S and the data sample points R1 and R2 in a principle configuration of the X-ray CT device of the present invention. In the X-ray CT device of the present configuration, it is designed such that the respective sizes in the X direction of detection elements P1, P2, P3, . . . that configure the X-ray detector 2 are reduced to one-half of the size in the same direction of the detection pixel P used in the general system shown in FIG. 30. In addition, in the X-ray CT device in the present example, a not shown signal addition circuit is provided, and it adds and outputs signals detected by two detection elements that are adjacent to each other in the X direction. Further, an addition position for adding the above-mentioned signals is changed at every image scanning timing. Specifically, at a certain image scanning timing, an addition of signals is performed in the form of P1+P2, P3+P4, . . . (hereinafter, referred to as an addition pattern 1) and is performed in the form of P2+P3, P4+P5, . . . (hereinafter, referred to as an addition pattern 2) at the next image scanning timing, and an image is captured while alternately repeating these two addition patterns. At that time, data sample points for the addition patterns 1 and 2 are respectively set as R1 and R2, and data of the sample interval ΔX/2 that is the same as that in the case of the FFS system shown in FIG. 31 can be acquired. Thereby, as in the case of the FFS, a reduction in spatial resolution caused by aliasing can be reduced by increasing the Nyquist frequency of a data sample to 2fn that is two times that of the general system.

In addition, since the S/N of the detection signal can be maintained equally to that of the detection signal by the general system by the signal addition, the above-mentioned high resolution measurement can be implemented without reducing the S/N. As shown in the present configuration example, in the X-ray CT device of the present invention, since image scanning can be performed while keeping the position of the X-ray generation point S fixed similarly to the general system, generation of the artifact that has been the problem in the FFS system can be prevented. In addition, since it is not necessary to utilize a special X-ray tube having a moving mechanics for the X-ray generation point position as in the case of the FFS system, the running cost of the X-ray CT device can be reduced.

Embodiment 1

A first embodiment is an embodiment of an X-ray CT device, that is, the X-ray CT device that generates a CT image of an object, including an X-ray generation unit, an X-ray detection unit that detects an X-ray image irradiated from the X-ray generation unit, a rotation mechanics unit that rotates the X-ray generation unit and the X-ray detection unit around the axis of rotaion, a signal read-out unit that reads out a signal detected by the X-ray detection unit at a predetermined image scanning timing, and a signal processing unit that processes a signal that has been output from the signal read-out unit to generate the CT image of the object, wherein the signal read-out unit adds and outputs signals detected by NX detection pixels that are adjacent in an X direction and/or Nz detection pixels that are adjacent in a z direction (here, NX and Nz are integers of 1 or more and either one of them is 2 or more) in the plurality of detection pixels configured in a matrix on an X-ray input plane of the X-ray detection unit, and performs changing of an addition position of the detection pixel where the addition is performed in synchronization with the image scanning timing, that is, executes relocation of the addition position.

Figure 1:
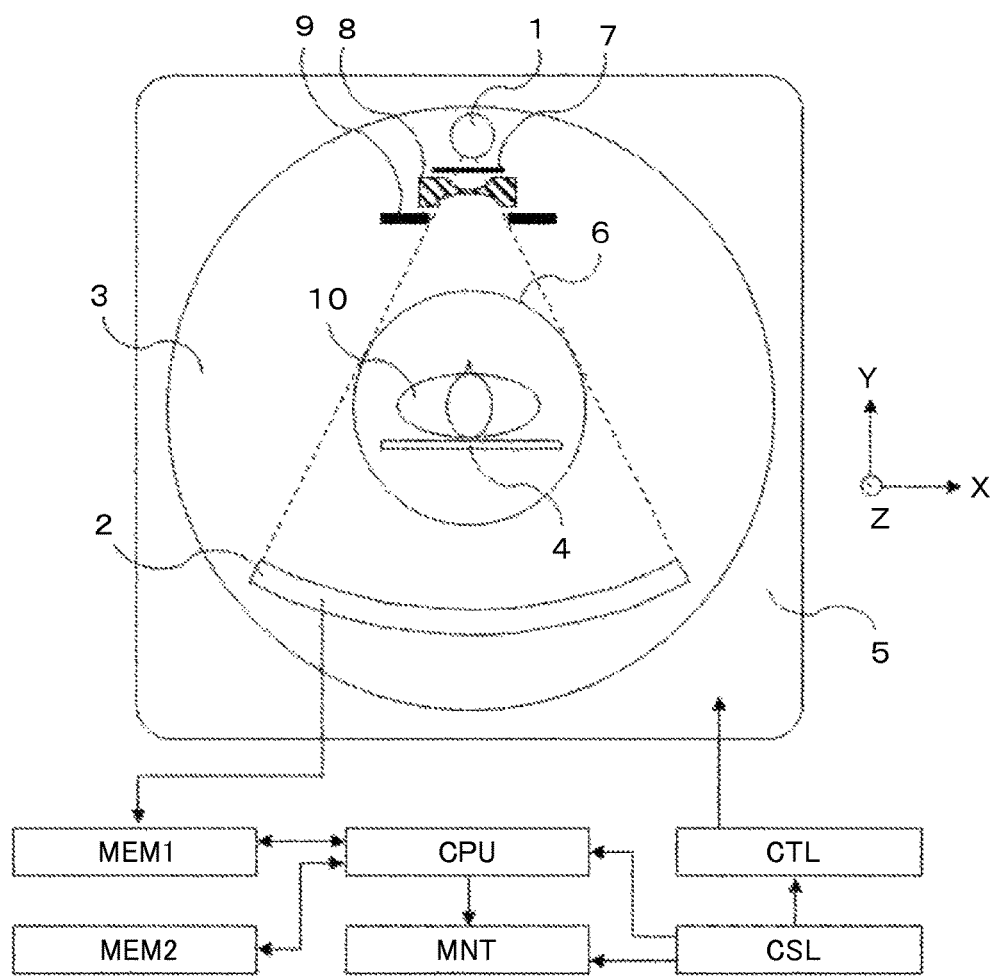
FIG. 1 is a front schematic diagram of an X-ray CT device, pertaining to a first embodiment.

FIG. 1 is a front schematic diagram of the X-ray CT device pertaining to the first embodiment. Incidentally, it is assumed that in FIG. 1, a left-right direction, an up-down direction and a vertical direction on a paper plane are respectively referred to as X, y and z directions. The X-ray CT device pertaining to the present embodiment is configured by an X-ray tube 1 that is an X-ray generation unit, an X-ray detector 2 that is an X-ray detection unit, a rotating plate 3 that is a rotation mechanics unit, a bed top plate 4, a gantry 5, a radiation quality filter 7, a bowtie filter 8, a collimator 9, a console CSL, an image scanning controller CTL, a computer CPU, a memory MEM1, a memory MEM2, and a monitor MNT and so forth. The X-ray tube 1, the radiation quality filter 7, the bowtie filter 8, the collimator 9, and the X-ray detector 2 are arranged on the rotating plate 3, and in the following, these will be generically called a rotational tomography system. The entire of the rotational tomography system is housed in the gantry 5. An opening 6 is provided in a central part of the gantry 5, and an object 10 is arranged in the vicinity of the center of the opening 6. The X-ray detector 2 in the present embodiment has a function of a signal read-out unit illustration of which is omitted in FIG. 1, in addition to a function as the above-mentioned X-ray detection unit in FIG. 1, as described in detail later by using FIG. 9, FIG. 11 to FIG. 15.

Incidentally, in the X-ray CT device of the present embodiment, a human body is supposed as the object 10, and the object 10 is generally arranged on the bed top plate 4 in a lying state. The rotating plate 3 that is the above-mentioned rotation mechanics unit is rotated by a not shown drive motor and captures X-ray transmission images from a whole circumferential direction of the object 10. The rotating plate 3 passes through the center of the opening 6 and rotates on the axis of rotation that is parallel with a z-axis. In addition, the position of the bed top plate 4 can be moved in the z-direction by a not shown drive. It is also possible to perform a well-known spiral scan by simultaneously performing rotation of the above-mentioned rotating plate 3 and movement of the above-mentioned bed top plate 4.

In FIG. 1, a representative example of the distance between the X-ray generation point of the X-ray tube 1 and the X-ray input plane of the X-ray detector 2 is 1040 [mm]. In addition, a representative example of the diameter of the opening 6 is 650 [mm]. A representative example of the rotating speed of the rotating plate 3 is 3 [rotation/sec], and the rotational tomography system captures the X-ray transmission images of the object 10 from various rotation angles. A representative example of the image scanning frequency in one rotation of the rotational tomography system is 1600 times, and one-time image scanning is performed while taking synchronization every time the rotating plate 3 rotates through 0.225 degrees.

The radiation quality filter 7 is a well-known one that is configured by superposing metal plates and so forth of a singular material or a multiple material. The radiation quality filter 7 is arranged in a path of an X-ray beam to be irradiated from the X-ray tube 1 toward the X-ray detector 2 and has a function of changing the radiation quality (an energy spectrum) of the X-ray after transmitted through the radiation quality filter 7. It is used for the purpose of reducing exposure of the object 10 and of reducing the influence of the BH effect by shielding low energy X-rays, in particular. As representative examples of the metal plates used for the radiation quality filter 7, there are a copper plate of about 0.05 to 0.2 mm in thickness and an aluminum plate of about several mm in thickness, or the one that they are superposed and so forth. Incidentally, in the X-ray CT device of the present embodiment, there are prepared a plurality of kinds of the radiation quality filters 7 such that a user can change the above-mentioned kind in accordance with the application of image scanning. At that time, the designated radiation quality filter 7 is arranged in the path of the X-ray beam prior to image scanning by a not shown movement mechanics.

The bowtie filter 8 is a well-known one formed by a material such as aluminum and so forth. The bowtie filter 8 is arranged in the path of the X-ray beam irradiated from the X-ray tube 1 toward the X-ray detector 2. The bowtie filter 8 has a shape that its thickness is changed such that a transmission path length of the above-mentioned X-ray beam in the bowtie filter 8 is the shortest at a central position of the opening 6 and becomes longer as it approaches a peripheral position. Thereby, the intensity of the X-ray that is incident upon the X-ray detector 2 after transmitted through the object 10 is equalized in an Xy-plane direction. As a result, there is such an effect that in the CT image of the object 10 to be finally obtained, the visibility of the CT image can be improved by equalizing graininess of noise on a central part and a peripheral part of the object. In addition, there is such an effect that the exposure at the peripheral position of the object 10 can be reduced. Incidentally, in the X-ray CT device of the present embodiment, for the bowtie filter 8, there are prepared ones having a plurality of shapes in accordance with the size of the object 10 and a part to be image scanned such that the user can change the above-mentioned kind. At that time, the designated bowtie filter 8 is arranged in the path of the X-ray beam prior to image scanning by the not shown movement mechanics.

The collimator 9 is a well-known X-ray shielding plate formed by a material such as lead and so forth and restricts X-ray irradiation ranges to be irradiated from the X-ray tube 1 in the Xy-plane direction and the z direction. The above-mentioned X-ray irradiation range in the Xy-plane direction is restricted so as to match an input range in the Xy-plane direction of the X-ray detector 2. In addition, the irradiation range in the z direction (hereinafter, referred to as a slice width) is made such that the use can change it in a variety of ways depending on the purpose of image scanning. At that time, the not shown movement mechanics moves the position of the collimator 9 to restrict the slice width to the designated size.

The X-ray detector 2 is a well-known one that is configured by an anti-scatter collimator 300, a scintillator array 303 and a photodiode array 304 and so forth that will be described later. The X-ray detector 2 has a two-dimensional input plane on which many X-ray detection elements have been arrayed in a matrix and is arranged such that the aforementioned input plane faces the X-ray tube 1. A representative example of the number of the aforementioned arrays is 2000 elements (the Xy-plane direction)×128 elements (the Z direction). The above-mentioned X-ray detection elements are arranged on an arc at almost equal intervals in the Xy-plane direction relative to the X-ray tube 1. A representative example of the size of each X-ray detection element in the Xy-plane direction and the z direction is 0.5 [mm].

Next, procedures of one series of operations of the X-ray CT device of the present embodiment upon image scanning will be described. First, the user instructs image scanning conditions through the console CSL and thereafter instructs to start image scanning. However, in the image scanning conditions, there are image scanning mode conditions peculiar to the present X-ray CT device, in addition to well-known conditions such as the tube voltage and the tube current of the X-ray tube 1, the rotating speed of the rotating plate 3, the slice width for image scanning, the kind of the radiation quality filter 7, the kind of the bowtie filter 8, the image scanning range of the object 10 and so forth. The user instructs the above-mentioned image scanning mode conditions in accordance with the purpose of image scanning and so forth to define the spatial resolution of the CT image to be finally measured by main image scanning. Incidentally, details of the image scanning mode conditions will be described later.

Next, at the same time that start of image scanning is instructed, the image scanning controller CTL starts rotation of the rotating plate. At the time point that the rotation of the rotating plate 3 has entered a constant speed state at the designated rotating speed, the image scanning controller CTL instructs X-ray irradiation of the X-ray tube 1 and start of the operation of the X-ray detector 2, and thereby image scanning is started. At that time, the X-ray detector 2 generates image scanning data while performing a pixel adding operation peculiar to the present X-ray CT device in accordance with the designated values of the above-mentioned image scanning mode conditions and outputs it. Incidentally, details of the above-mentioned pixel adding operation of the X-ray detector 2 will be described later.

The image scanning data that has been output from the X-ray detector 2 is transmitted from the rotational tomography system to a static system, that is, a non-rotational system in the gantry 5 via a not shown well-known optical slip ring and thereafter is temporarily stored into the memory MEM1. At the same time that the image scanning data is stored into the memory MEM1, the computer CPU sequentially performs a later described preprocessing operation on the above-mentioned image scanning data and stores a result into the memory MEM2. Incidentally, in the above-mentioned preprocessing operation, reference data that has been stored in advance in the memory MEM2 is referred by the computer CPU. Incidentally, contents of the above-mentioned preprocessing operation and details of the reference data will be described later. Next, the computer CPU reads out the above-mentioned image scanning data after preprocessed from the memory MEM2, reconstructs the CT image of the object 10 by using a well-known reconstruction algorithm and stores data on the CT image obtained as a result thereof into the memory MEM2.

In addition, the computer CPU reads out the data on the above-mentioned CT image from MEM2, thereafter creates a display image of the above-mentioned CT image by using well-known image processing techniques such as a volume rendering method, an MIP (Maximum Intensity Projection) method, an MPR (Multi Planar Reconstruction) method and so forth and displays the created display image on the screen of the monitor MNT. Incidentally, in FIG. 1, a dedicated arithmetic unit or a well-known general-purpose arithmetic unit and so forth is used for the computer CPU. In addition, there are used well-known recording means such as a RAM (Random Access Memory) for the memory MEM 1, and a hard disk, an SSD (Solid State Drive) and so forth for the memory MEM 2 and combinations thereof and so forth.

Figure 2:
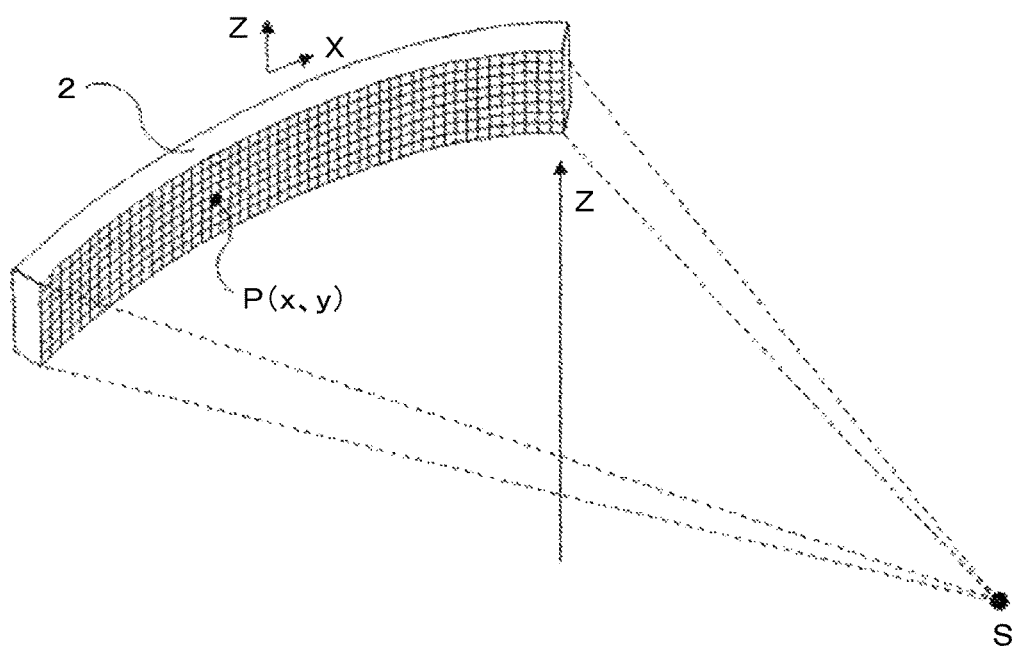
FIG. 2 is a perspective view for describing a positional relation between an X-ray focal point S of an X-ray tube and an X-ray detector, pertaining to the first embodiment.

FIG. 2 is a perspective view for describing a positional relation between the X-ray focal point S of the X-ray tube 1 and the X-ray detector 2 of the present embodiment. On the input plane of the X-ray detector 2, many X-ray detection elements are arrayed in a matrix, and hereinafter, a unit detection region of the X-ray detector 2 formed by each X-ray detection element will be called a detection pixel and denoted by P(X, z). However, it is supposed that X, z indicates the position of the detection pixel, X is a direction vertical to the Z-axis and z is a direction parallel with the Z-axis.

Figure 3:
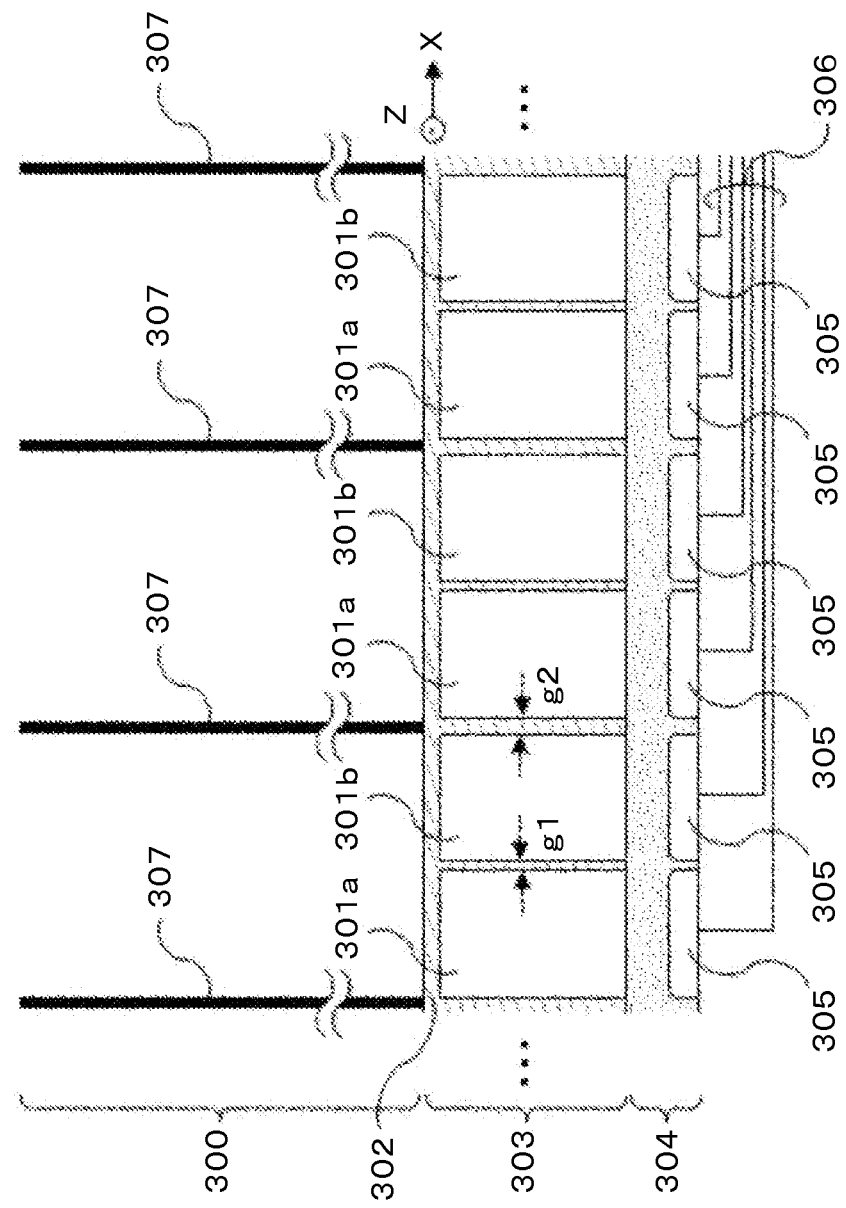
FIG. 3 is a sectional diagram for describing a sectional structure in an X direction of the X-ray detector, pertaining to the first embodiment.

FIG. 3 is a sectional diagram for describing a sectional structure in the X direction of the X-ray detector 2 of the present embodiment. The X-ray detector 2 is configured by the scattering ray removing collimator 300, the scintillator array 303, the photodiode array 304 and so forth. The scintillator array 303 is configured by a scintillator block 301 and a light reflector 302. The scintillator blocks 301 are formed by a well-known scintillator material that converts light into X-rays and are arranged in a matrix in the X direction and the z direction. A gap between the respective scintillator blocks 301 and upper surfaces thereof are filled with the light reflector 302 formed by a well-known material. The light reflector 302 has a function of reflecting light generated in the scintillator block 301 at an interface between the scintillator block 301 and the light reflector 302 and is used to prevent occurrence of a reduction in spatial resolution caused by crosstalk due to incidence of the above-mentioned light upon the adjacent scintillator blocks 301. In addition, the light reflector 302 has a function of preventing attenuation of the above-mentioned optical signal caused by the above-mentioned crosstalk and radiation of light from the upper surface of the scintillator block 301. Further, the light reflector 302 has a function as an adhesive that adheres and fixes together the scintillator blocks 301. The scattering ray removing collimator 300 that is formed by a well-known material is arranged on the upper surface of the scintillator block 303. The scattering ray removing collimator 300 has a grid-shaped form when observed from an upper part of this drawing that is vertical to the Xz-plane, and therefore the sectional diagrams in the X direction and the z direction each has a form that looks as if many slits 307 are arrayed in each direction as in this drawing.

Incidentally, although in the X-ray CT device of the present embodiment, the slits 307 are arranged above every other gap in the X direction between scintillator blocks 301$a$ and 301$b$, it is not limited thereto, and they may be arranged above all gaps, every three ones, every four ones and so forth. In addition, since the incident X-ray is shielded by the above-mentioned slit in the gap having the slit 300 above it, the crosstalk occurred between the above-mentioned gaps can be reduced by setting a distance g2 of that gap as large as possible in the above-mentioned shielded area. On the other hand, in a gap not having the slit 300 above it, a reduction in utilization efficiency of the X-ray can be prevented by setting a distance g1 of that gap comparatively small. Incidentally, the slits 307 are arranged so as to respectively direct to the X-ray focal point S shown in FIG. 2. Owing to the above structure, the scattering ray removing collimator 300 has a function of shielding scattering X rays that are incident upon the input plane of the X-ray detector 2 in the X direction and the z direction at a comparatively large incidence angle, in scattering X rays that enter the X-ray detector 2 after scattered in the object 10 or the like. A reduction in S/N of a CT reconstructed image to be finally generated by the present X-ray CT device and a reduction in precision of a CT value can be prevented by removing such scattering X-rays.

The photodiode array 304 is a well-known back side irradiation type photodiode array formed on a silicon substrate, and photodiode elements 305 are formed in an array in the Xz-plane direction in the above-mentioned substrate. Incidentally, each of the above-mentioned photodiode elements 305 is designed such that its position in the Xz-plane direction matches that of each of the scintillator blocks 301a and 301b. Light generated in each of the scintillator blocks 301a and 301b is incident upon the photodiode element 305 from a lower surface thereof, then is converted into an electric signal and then is output via an output signal line 306. Although the sectional structure in the X direction of the X-ray detector 2 has been described hereinabove, since the sectional structure in the z direction is the same as that in the X direction, description thereof is omitted.

Figure 4:
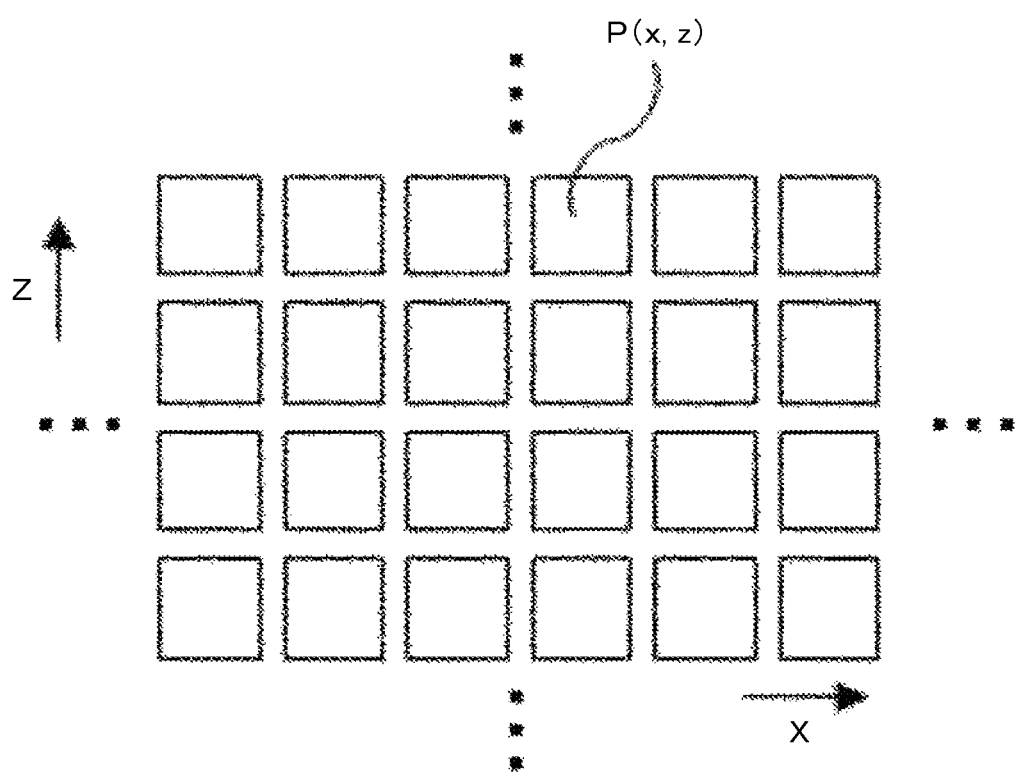
FIG. 4 is a diagram for describing an arrangement of detection pixels P(X, z) viewed from the input plane side of the X-ray detector, pertaining to the first embodiment.

FIG. 4 is a diagram for describing an arrangement of the detection pixels P(X, z) when viewed from the input plane side of the X-ray detector 2. However, in FIG. 4, the symbol P(X, z) is displayed on only representative one of the detection elements that are present in plural for simplicity of the drawing. As shown in the present drawing, the detection pixels P(X, z) are arranged in a matrix in the X direction and the z direction. In addition, each detection pixel P(X, z) is a unit detection region individually formed by a pair of single elements of the scintillator block 301 and the photodiode element 305 shown in FIG. 3.

Figure 5:
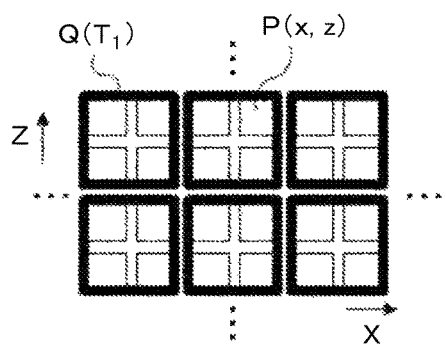
FIG. 5 is diagrams for describing a pixel adding operation peculiar to the X-ray CT device, pertaining to the first embodiment.
Figure 5:
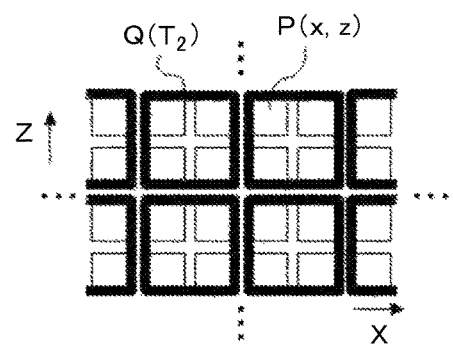
Figure 5:
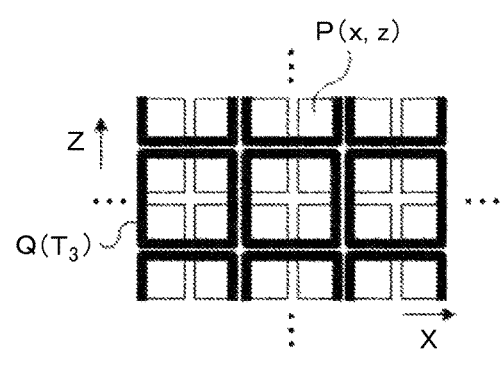
Figure 5:
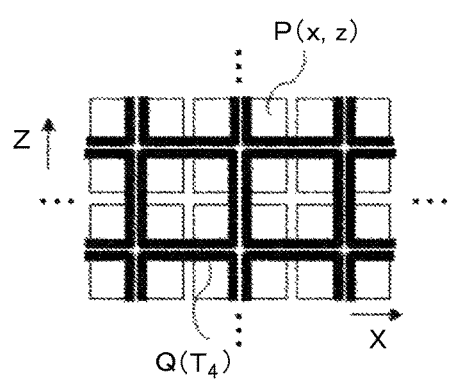

FIG. 5 is diagrams for describing a pixel adding operation peculiar to the X-ray CT device of the present embodiment. In the X-ray CT device of the present embodiment, when performing a plurality of image scanning operations from various directions on the object 10 while rotating the rotational tomography system, signals detected by the plurality of detection pixels P(X, z) of the X-ray detector 2 are pixel-added and measured. In addition, it has such a characteristic that an addition position Q for the above-mentioned pixel addition is changed synchronously at every image scanning timing of the above-mentioned plurality of image scanning operations.

Although, in FIG. 5, there is shown an example that, the above-mentioned pixel addition, every two pixels in the X and the z directions, that is, four detection pixels in total are added together, it goes without saying that it is not limited to this. In addition, in FIG. 5, there is shown an example that the addition position Q for the above-mentioned pixel addition is shifted detection-pixel by detection-pixel respectively in the X and z direction at every image scanning timing. At that time, four different variations in total are present for the addition position Q and respective addition positions $Q(T_1)$ to $Q(T_4)$ (wherein it is assumed that $T_1$ to $T_4$ denote four different image scanning timings) are respectively shown in (A) to (D) of FIG. 5. It is assumed that thick-lined squares shown in FIG. 5 all indicate the addition positions Q and the detection pixels P(X, z) that are present in a region surrounded by this thick line are added. In addition, in (A) to (D) of FIG. 5, the symbols $Q(T_1)$ to $Q(T_4)$ are displayed on only representative ones of the addition positions (thick lines) that are present in plural for simplicity of the drawing in (A) to (D) of FIG. 5.

Incidentally, (A) to (D) of FIG. 5 merely show examples of changing of the addition position corresponding to the four different image scanning timings $T_1$ to $T_4$ and it is not limited to this, and the addition position Q may be changed in other ways corresponding to the image scanning timings $T_1$ to $T_4$. For example, it is also possible to perform changing of the addition position only in an oblique direction in FIG. 5 in such a manner that the addition positions shown in (A) of FIG. 5 and (D) of FIG. 5 are alternately repeated at the continuous image scanning timings.

In the following, numbers of added ones in the X and z directions in the pixel addition are generally denoted respectively by NX and Nz. In addition, shift amounts of the addition position in the X and z directions are respectively denoted by MX and Mz. At that time, a number G of variations of the addition positions for the pixel addition is indicated by the following Formula 1.

$$G=(UX/MX)*(Uz/Mz) \text{ (wherein } 1 \le MX, 1 \le Mz) \qquad \text{(Formula 1)}$$

wherein UX denotes the least common multiple of NX and MX and Uz denotes the least common multiple of Nz and Mz.

For example, examples of the pixel addition shown in FIG. 5 can be expressed as NX=2, Nz=2, MX=1, Mz=1. At that time, G=4 from Numerical Formula 1. In the following, pixel addition conditions defined by the values of NX, Nz, MX, Mz as mentioned above will be called image scanning mode conditions. Incidentally, in a case where the value of NX or Nz is 1, it is regarded that the pixel addition in each direction is not performed (the number of added ones 1). In addition, in a case where the value of MX or Mz is 0, it is regarded that there is no shift of the pixel addition position in each direction (the shift amount 0) and U/M=1 is set in Numerical Formula 1. Incidentally, as already described, since over-sampling on the added pixels can be implemented by setting as MX<NX, Mz<Nz, there is such an advantage that a reduction in spatial resolution caused by aliasing can be reduced.

Figure 6:
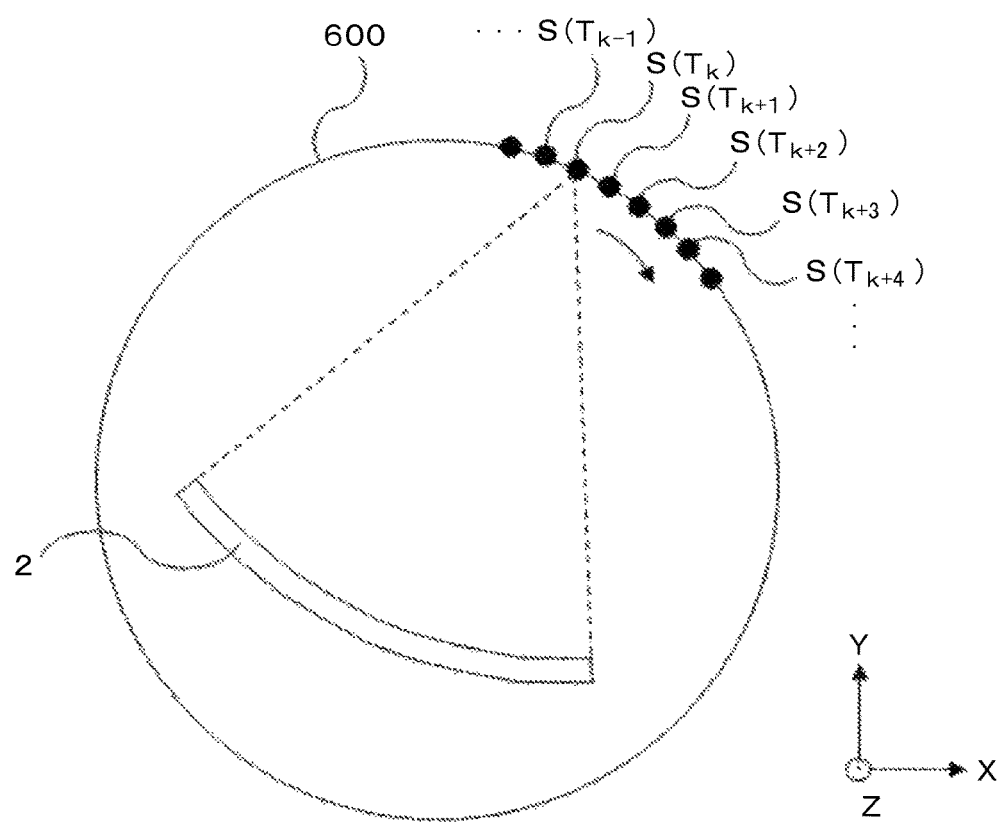
FIG. 6 is a diagram for describing a relation between an image scanning timing and a pixel addition position, pertaining to the first embodiment.

FIG. 6 is a diagram for describing a relation between the image scanning timing and the pixel addition position in the X-ray CT device of the present embodiment. In FIG. 6, $S(T_k)$ denotes a position of the X-ray generation point at an image scanning timing $T_k$. The position of the X-ray generation point S is sequentially changed to $S(T_k)$, $S(T_{k+1})$, $S(T_{k+2})$, . . . on a circle 600 with rotation of the rotational tomography system. Simultaneously with this, in the X-ray detector 2, the pixel addition position is sequentially changed in the cycle G such as $Q(T_1)$, $Q(T_2)$, . . . $Q(T_G)$, $Q(T_1)$, $Q(T_2)$, . . . in conjunction with changing of the above-mentioned image scanning timing. Cyclic position changing is performed for every frame of image scanning while synchronizing this image scanning timing with a pixel addition position switching timing. For example, in the example of the pixel addition shown in FIG. 5, changing of positions of four cycles of $Q(T_1)$, $Q(T_2)$, $Q(T_3)$, $Q(T_4)$, $Q(T_1)$, $Q(T_2)$, . . . is repeated.

Figure 7:
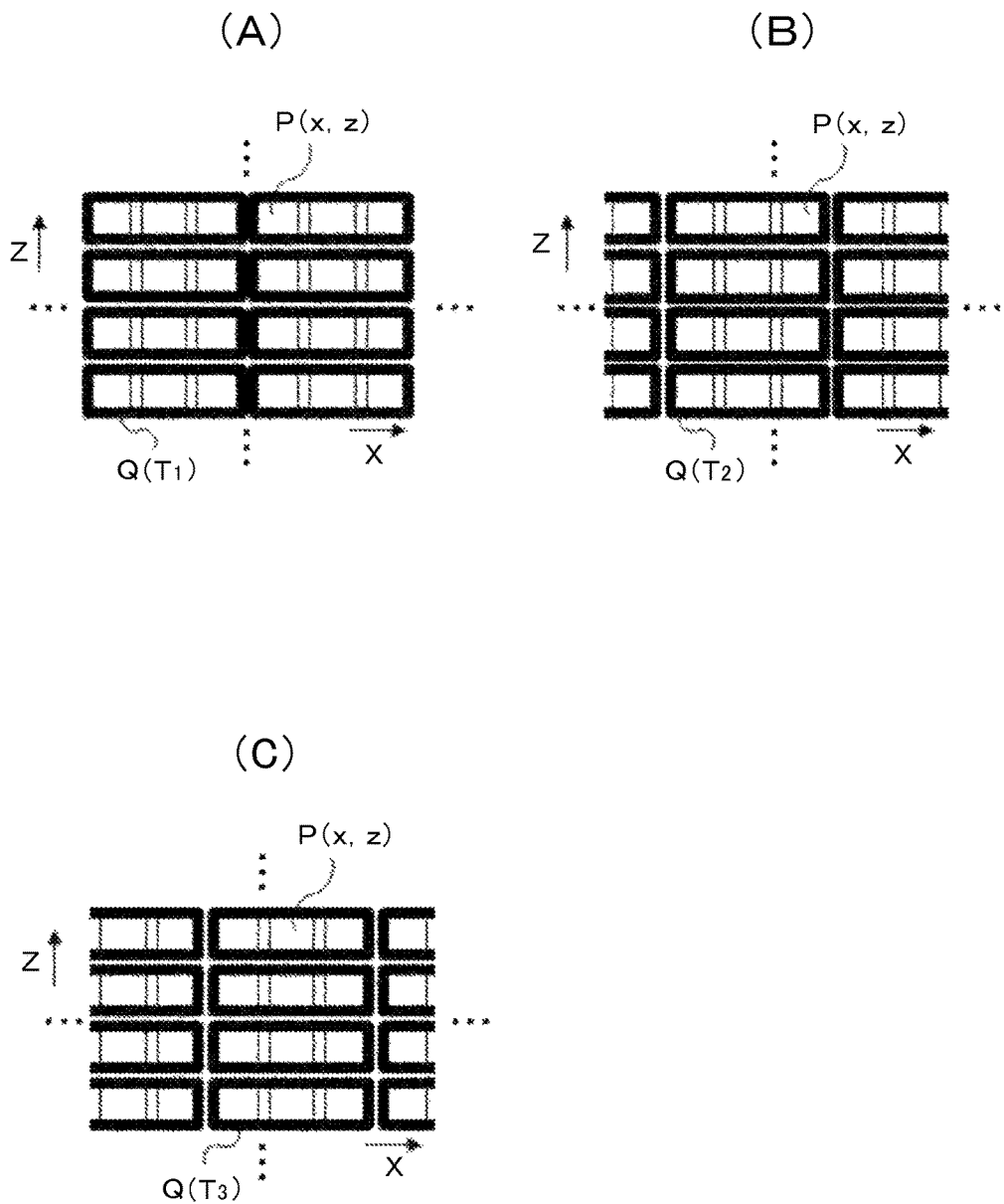
FIG. 7 is diagrams for describing another example of pixel addition, pertaining to the first embodiment.

FIG. 7 is diagrams for describing another example of the pixel addition. In this example, patterns under the image scanning mode conditions NX=3, Nz=1, MX=1, Mz=0 are shown. At that time, G=3 from Numerical Formula 1, and the respective addition positions $Q(T_1)$ to $Q(T_3)$ at the respective image scanning timings are respectively shown in (A) to (C) of FIG. 7. However, in (A) to (C) of FIG. 7, the symbols $Q(T_1)$ to $Q(T_3)$ are displayed on only representative ones of the addition positions (the thick lines) that are present in plural for simplicity of the drawing. As shown in this drawing, the pixel addition and addition position shifting in the z direction are not performed because of Nz=1, Mz=0. On the other hand, the addition position is changed with a shift amount (1 pixel) that is ⅓ of the number of added ones (3 pixels) in the X direction. In this case, since the Nyquist frequency in the X direction is increased by three times in comparison with a case where the addition position is not changed, the reduction in spatial resolution caused by aliasing can be further reduced in comparison with the example (the Nyquist frequency is increased by two times) shown in FIG. 5.

Figure 8:
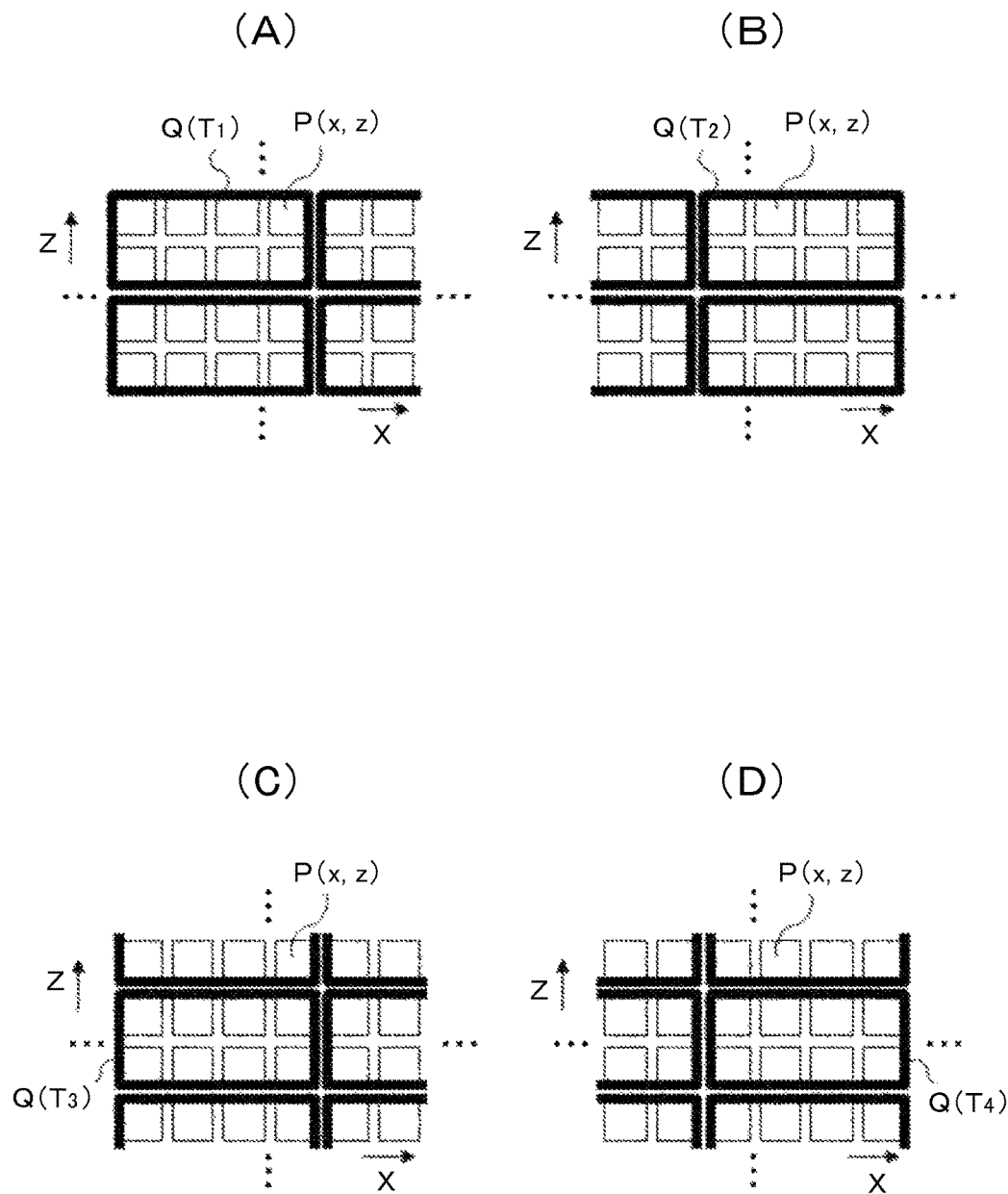
FIG. 8 is diagrams for describing a further another example of the pixel addition, pertaining to the first embodiment.

FIG. 8 is diagrams for describing a further another example of the pixel addition. In this example, patterns under the image scanning mode conditions NX=4, Nz=2, MX=2, Mz=1 are shown. At that time, G=4 from Numerical Formula 1 and the respective addition positions $Q(T_1)$ to $Q(T_4)$ at the respective image scanning timings are respectively shown in (A) to (D) of FIG. 8. However, in (A) to (D) of FIG. 8, the symbols $Q(T_1)$ to $Q(T_4)$ are displayed on only representative ones of the addition positions (the thick lines) that are present in plural for simplicity of the drawing. Although there are cases when the time resolution is more preferred than the spatial resolution depending on the purpose of image scanning, the number of added ones may be set large as in the drawing in such a case. At that time, since the total number of added pixels is reduced and the amount of signals to be output from the X-ray detector 2 is reduced, it becomes possible to cope with the improvement in time resolution by increasing the frame rate of the image scanning.

Figure 9:
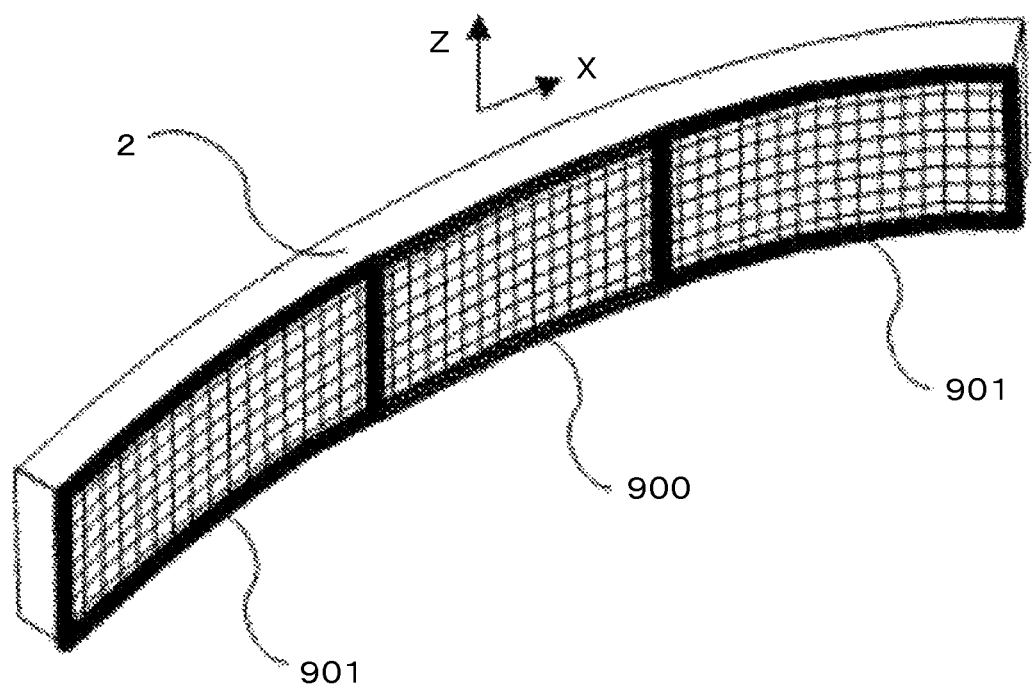
FIG. 9 is a diagram for describing a detector central area and a detector peripheral area set on the X-ray detector, pertaining to the first embodiment.

FIG. 9 is a diagram for describing a detector central area 900 and a detector peripheral area 901 set on the X-ray detector 2 of the present embodiment. The image scanning mode conditions may be individually set for every area that has been set, for example, as mentioned above. For example, in a case where the lug blood vessel of the object 10 is to be diagnosed, since measurement of high spatial resolution is demanded over the entire viewing field of image scanning, the image scanning mode conditions may be set as NX=2, Nz=2, MX=1, Mz=1 and so forth for both of the detector central area 900 and the detector peripheral area 901. In addition, in a case where the lumen in the coronary stent is to be evaluated, since a region of interest is limited to only the central vicinity of the viewing field of image scanning, the image scanning mode conditions for the detector central area 900 may be set as NX=1, Nz=1, MX=0, Mz=0 and the image scanning mode conditions for the detector peripheral area 901 may be set as NX=3, Nz=3, MX=0, Mz=0 and so forth. Incidentally, setting of areas in the detector is not limited to the present example and the number and the positions thereof may be changed in a variety of ways.

Figure 10:
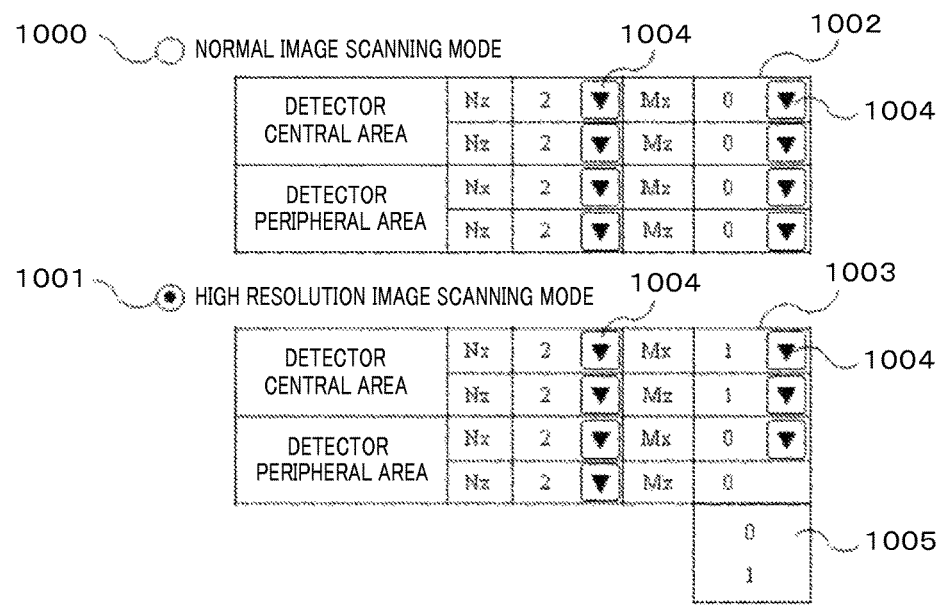
FIG. 10 is diagrams showing one example of a setting screen for setting image scanning mode conditions, pertaining to the first embodiment.

FIG. 10 is diagrams showing examples of a setting screen that functions as a designation unit for setting the image scanning mode conditions. Incidentally, it is assumed that the present setting screen is displayed, for example, on the monitor MNT in FIG. 1 and various set values are input by using well known information input means such as a keyboard, a mouse and so forth from the console CSL. It goes without saying that it is also possible to provide the setting screen on the console CSL and so forth.

In the example shown in the present drawing, as image scanning modes, a normal image scanning mode and a high resolution image scanning mode are prepared, and the user can select the image scanning mode through selection of radio buttons 1000 and 1001 in accordance with the purpose of image scanning. For each image scanning mode, input lists 1002 and 1003 for setting values of NX, Nz, MX and Mz that are the image scanning mode conditions are prepared and values of individual ones are preset. In addition, the above-mentioned image scanning mode conditions are made to be pre-settable for both of the detector central area 900 and the detector peripheral area 901. Incidentally, it is also possible to change each preset value by the user. When changing the above-mentioned preset value, it is made such that the user can select a target set value from within a selection list 1005 that is displayed at that time by depressing a pull-down button 1004. In other words, it is made possible to individually set NX, Nz and so forth for the detector central area and the detector peripheral area that are the plurality of different small regions that have been set in advance in a detection region of the X-ray detector 2 that is the X-ray detection unit. Incidentally, a method of setting the image scanning mode conditions for every area is not limited to the present example and it may be substituted for well-known various methods.

Figure 11:
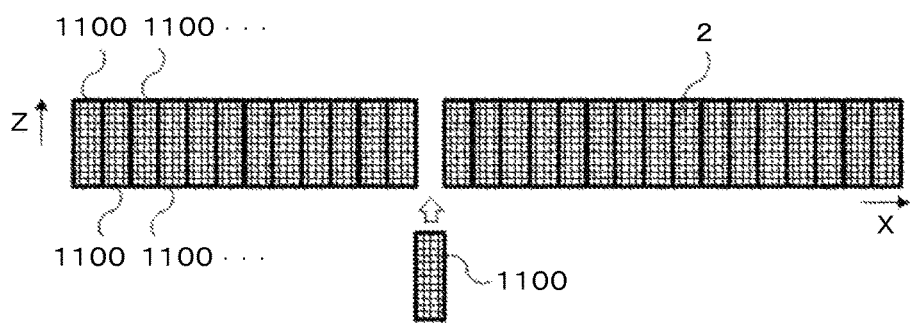
FIG. 11 is a diagram for describing an arrangement of detector modules that configure the X-ray detector, pertaining to the first embodiment.

FIG. 11 is a diagram for describing an arrangement of detector modules 1100 that configure the X-ray detector 2 in the X-ray CT device of the present embodiment. As shown in the present drawing, the X-ray detector 2 is formed by arraying the detector modules 1100 in plural in the X direction. In the present specification, this detector module is called a small detector for convenience. By configuring in this way, even in a case where a fault such as a pixel defect has occurred in some detection pixels of the X-ray detector 2, low-cost repair becomes possible by replacing only the detector module 1100 that is the small detector concerned. In addition, although the detector modules 1100 the X-ray input plane of each of which has a planar shape are generally used, the X-ray detector 2 having an almost arc-shaped input plane such as that shown in FIG. 2 can be formed by arranging these small detectors on frames on the not shown same arc that is centered at the X-ray focal point S.

Figure 12:
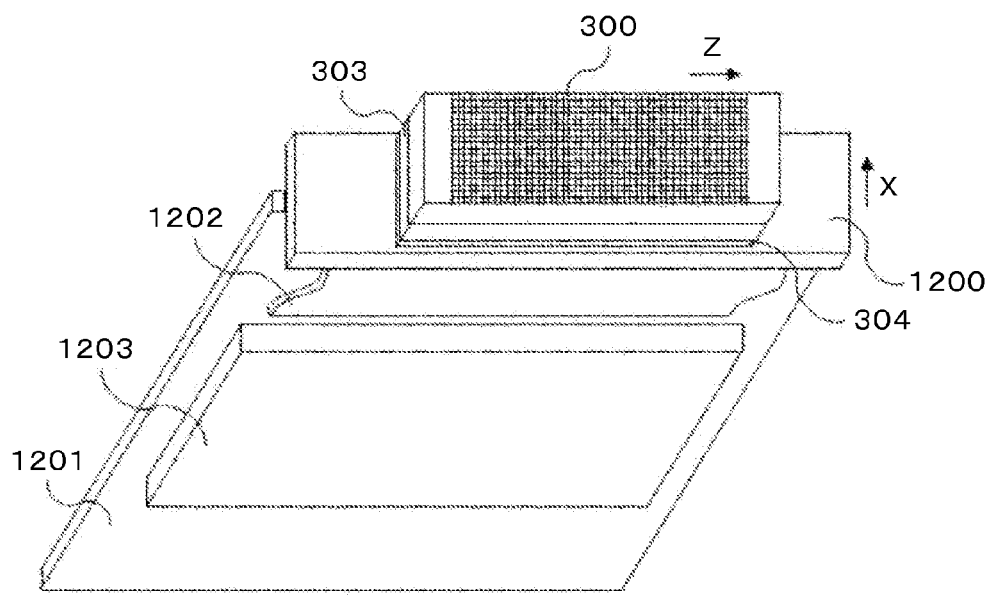
FIG. 12 is a perspective view for describing one example of a structure of the detector module, pertaining to the first embodiment.

FIG. 12 is a perspective view for describing one concrete example of a structure of the small detector that configures the X-ray detector 2, that is, each detector module 1100 in the X-ray CT device of the present embodiment. The detector module 1100 is configured by the scattering ray removing collimator 300, the scintillator array 303, the photodiode array 304, a substrate 1200, a substrate 1201, flexible wiring 1202, a DAS (Data Acquisition System) chip 1203 and so forth. This DAS chip 1203 functions as a signal read-out unit of the above-mentioned present embodiment.

As described in FIG. 3, the scintillator array 303 is arranged on the upper surface of the photodiode array 304 and further the scattering ray removing collimator 300 is arranged on the upper surface of the scintillator array 303. In addition, the photodiode array 304 is fixed onto an upper surface of the substrate 1200, and the substrate 1201 is fixed onto a back surface of the substrate 1200 such that a substrate plane thereof becomes vertical. The output signal line 306 of the photodiode array 304 shown in FIG. 3 is connected to the flexible wiring 1202 one end of which has been fixed to the back surface side of the substrate 1200 via a not shown through-hole formed in the substrate 1200. In addition, the other end of the flexible wiring 1202 is fixed onto the substrate 1201 and is connected to the DAS chip 1203 via a not shown terminal formed on the substrate 1201. The DAS chip 1203 is a circuit that AD (Analog-to-Digital)-converts an electric signal output from the photodiode array 304 and outputs it as a digital signal, and is formed by using a well-known CMOS technology and so forth.

Outputs from the plurality of DAS chips 1203 corresponding to the plurality of detector modules 1100 are stored into the memory MEM1 as image scanning data and are subjected to signal processing by the computer CPU that is a signal processing unit, and the CT image of the object is generated. Incidentally, the structure of the detector module 1100 that is the small detector is not limited to that in the present example. For example, the DAS chip 1203 may be directly connected and fixed onto a silicon substrate on which the back side irradiation type photodiode array 304 is formed by using a well-known technique such as flip chip bonding and so forth.

Figure 13:
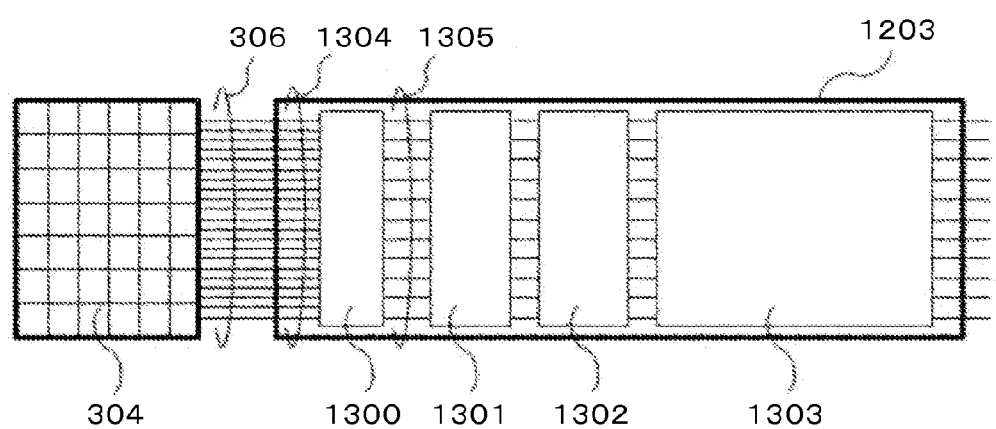
FIG. 13 is a diagram for describing one example of the outline of a circuit configuration of a DAS chip that is a signal read-out unit, pertaining to the first embodiment.
Figure 14:
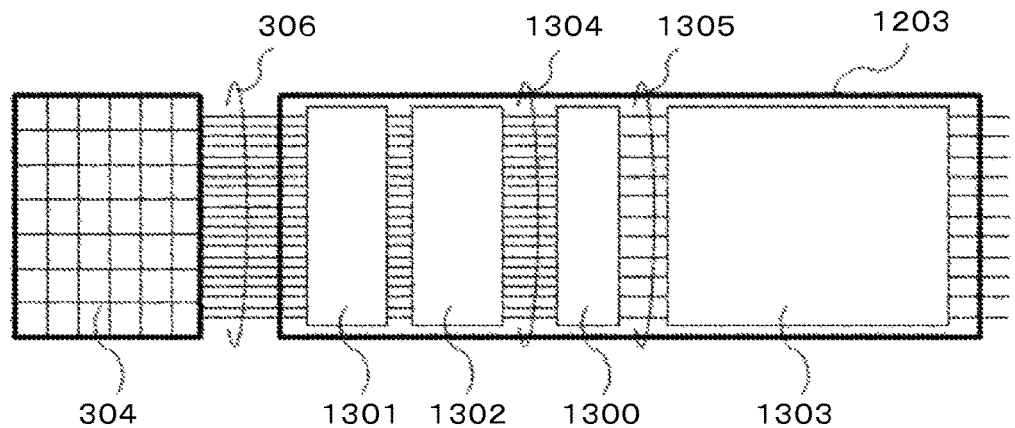
FIG. 14 is a diagram for describing another example of the outline of the circuit configuration of the DAS chip that is the signal read-out unit, pertaining to the first embodiment.
Figure 15:
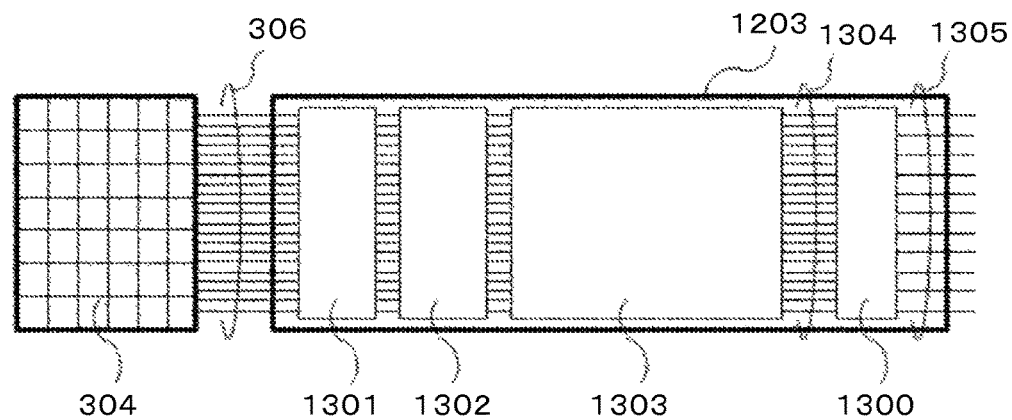
FIG. 15 is a diagram for describing a further another example of the outline of the circuit configuration of the DAS chip that is the signal read-out unit, pertaining to the first embodiment.

Each of FIGS. 13 to 15 is a circuit diagram for describing the outline of a circuit configuration of the DAS chip 1203 that is a signal read-out unit in the X-ray CT device of the present embodiment. A circuit in the DAS chip 1203 that is the signal read-out unit is mainly configured by a pixel addition circuit 1300, a CA (Charge Amplifier) circuit array 1301, an SH (Sample Hold) circuit array 1302, an ADC (Analog-to-Digital Converter) circuit array 1303 and so forth. Although, among these, the CA circuit array 1301, the SH circuit array 1302 and the ADC circuit array 1303 are arranged in the above-mentioned order from a signal input direction toward an output direction (from a left direction toward a right direction in the drawing) in all of the circuit configurations shown in FIGS. 13 to 15, the position of the pixel addition circuit 1300 is made different in each of them.

That is, the pixel addition circuit 1300 is arranged at the first stage (the front stage of the CA circuit array) in the example in FIG. 13, is arranged between the SH circuit array 1302 and the ADC circuit array 1303 in the example in FIG. 14 and is arranged at the last stage (the rear stage of the ADC circuit array 1303) in the example in FIG. 15. The CA circuit array 1300 is the one that well-known charge amplifiers adapted to accumulate charge signals generated by the photodiode array 304 and convert them into voltage signals are formed in a parallel array for every input signal line. In addition, the SH circuit array 1302 is the one that well-known sample hold circuits adapted to sample output voltages of the charge amplifiers at a predetermined timing are formed in a parallel array for every input signal line. Incidentally, a timing of sampling of this sample hold circuit becomes the image scanning timing of the X-ray CT device. Further, the ADC circuit array 1303 is the one that well-known ADC circuits adapted to convert the voltage signals that have been sampled by the above-mentioned sample hold circuits into digital signals are formed in a parallel array for every input signal line. The pixel addition circuit 1300 is a circuit for performing the pixel addition that has already been described.

Although in the X-ray CT device of the present embodiment, NX and Nz can be set as the numbers of added ones in the pixel addition as described by using FIG. 10, in a case where either one of values of minimum values $NX_0$ and $Nz_0$ that can be set as NX and Nz is 2 or more, since an addition of signals is surely performed by the pixel addition circuit 1300, the number of output signal lines 1305 of the pixel addition circuit 1300 can be reduced relative to the number of the input signal lines 1304 thereof. Thus, the more the pixel addition circuit 1300 is at an upper stage, the more the number of succeeding parallel circuits can be reduced. Such a reduction in number of circuits has such advantages that the power consumption of the circuit is suppressed to reduce heat generation from the circuit and the production yield of the DAS chip 1203 can be improved.

Since the pixel addition circuit 1300 is arranged at the uppermost stage in the circuit configuration example shown in FIG. 13, there is such a merit that the number of succeeding circuits can be reduced the most. However, on the other hand, there is also such a demerit that it is the most liable to be influenced by circuit noise generated in association with the pixel addition. On the other hand, in the circuit configuration example shown in FIG. 14, the pixel addition circuit 1300 is arranged at the intermediate stage and it is necessary to form the CA circuit array 1301 and the SH circuit array that are at the front stage in parallel by the same number as that of the output signal lines 306 of the photodiode array 304. However, since the signal is added after the signal has been amplified by the CA circuit array 1301, there is such a merit that it is hardly influenced by the circuit noise generated upon the addition in comparison with the case in FIG. 13. In addition, there is also such a merit that the amount of circuits in the ADC circuit array 1303 that is the highest in power consumption and heat generation amount can be reduced. Incidentally, for the pixel addition circuit 1300 in FIG. 14, a well-known addition circuit that adds voltage signals to be output from the S/H circuit array 1302 is used. On the other hand, in the circuit configuration example shown in FIG. 15, the pixel addition circuit 1300 is arranged at the rearmost stage and there is such a demerit that the amount of circuits cannot be reduced. However, since the signals are added after converted into digital signals by the ADC circuit array 1303, there is such a merit that there is no generation of the circuit noise incidental to the addition. Incidentally, for the pixel addition circuit 1300 in FIG. 15, a well-known digital addition circuit is used.

Figure 16:
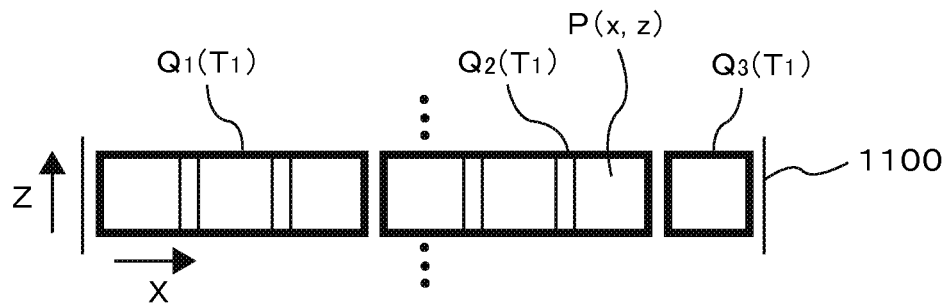
FIG. 16 is diagrams for describing an addition position Q for a pixel addition performed in each detector module, pertaining to the first embodiment.
Figure 16:
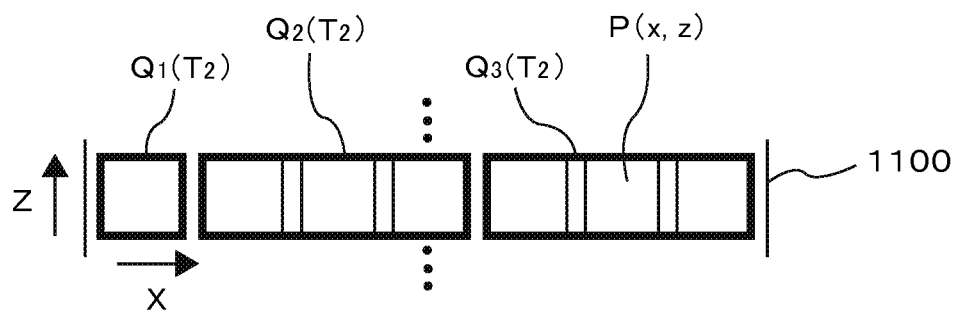
Figure 16:
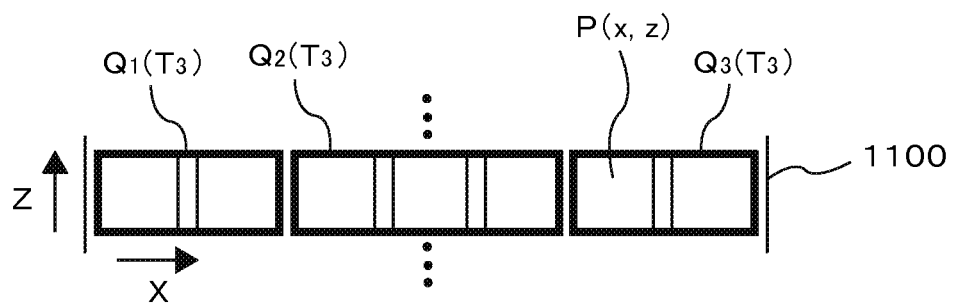

FIG. 16 is schematic diagrams for describing the addition position Q for the pixel addition to be performed in each of the detector modules 1100. In each of the detector modules 1100, since the detection pixels P(X, z) to be arrayed in the X direction and the z direction are limited, there are cases when the numbers of added ones do not reach NX and Nz at ends in the respective directions when performing the pixel addition. Thus, such a case occurs that the number of signals to be output after added is changed depending on the image scanning timing. On the other hand, as described in FIGS. 12 to 15, since the DAS chip 1203 as the signal read-out unit having the pixel addition circuit 1300 is individually prepared for every detector module, a pixel adding ability to parallel-process them in the pixel addition circuit 1300, and the number of the output signal lines 1304 through which they are output after added should be in a state of being set to a maximum value of the above-mentioned number of output signal lines. Now, it is assumed that the numbers of the detection pixels P(X, z) that each detector module 1100 has in the X direction and the z direction are respectively denoted by KX and Kz.

The example shown in FIG. 16 is a case where the image scanning mode conditions have been set as NX=3, Nz=1, MX=1, Mz=0 when KX=7. At that time, G=3 from Numerical Formula 1, and the respective addition positions $Q(T_1)$ to $Q(T_3)$ at the respective image scanning timings are respectively shown in (A) to (C) of FIG. 16. In addition, in FIG. 16, the respective addition positions are numbered in the form of $Q_1(T)$, $Q_2(T)$, . . . in order from the left side. As shown in (A) to (C) of FIG. 16, in the present example, a maximum value of the number assigned by the above-mentioned numbering is 3 and a maximum value of the number of signals to be output in the X direction becomes 3. If the maximum value of the number of signals to be output in the X direction is denoted by LX like this, LX can be calculated by the following Formulae 2, 3 and 4.

(1) In a case where NX is 2 or more and MX is 1 or more, LX=JX+1 (in a case where IX=0, or IX=1, or IX=MX and NX is a multiple of MX)

$$LX=JX+2 \text{ (a case other than the above)} \qquad \text{(Formula 2)}$$

(2) In a case where NX is 1

$$LX=KX \qquad \text{(Formula 3)}$$

(3) In a case where MX is 0

$$LX=JX \text{ (in a case where } IX=0\text{), } LX=JX+1 \text{ (in a case where } IX \neq 0\text{)} \qquad \text{(Formula 4)},$$

wherein, it is assumed that in the Formula 2 and the Formula 4, KX=NX×JX+IX (IX is an integer that meets 0≤IX≤NX).

For example, when the image scanning mode conditions NX=3, MX=1 in FIG. 16 are substituted into Numeral Formula 2, LX=3 and it matches the above-mentioned result. Likewise, when the subscript X is changed to z in Numeral Formulae 2 to 4, a maximum value Lz of the number of signals to be output in the z direction can be calculated. At that time, the maximum value of the number of the output signal lines 1304 through which they are output from the pixel addition circuit 1300 becomes LX×Lz.

Figure 17:
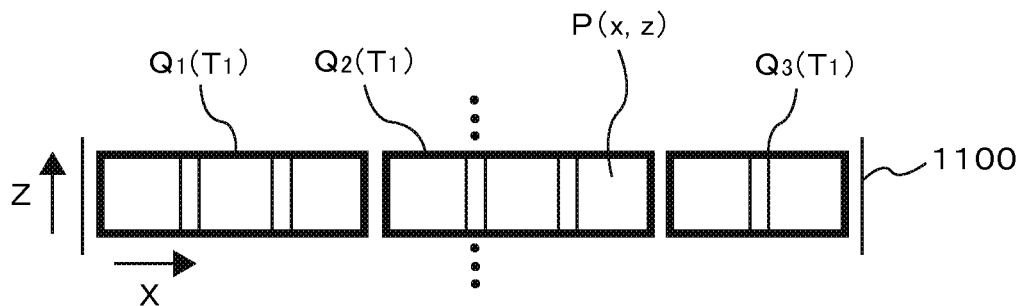
FIG. 17 is diagrams for describing another example of the pixel addition performed in each detector module, pertaining to the first embodiment.
Figure 17:
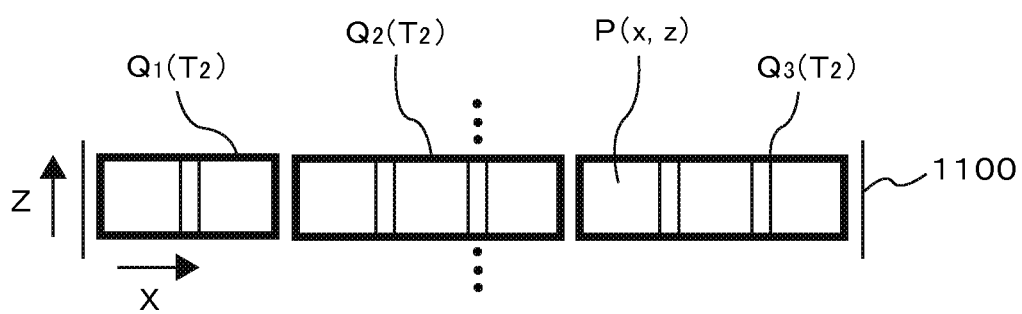
Figure 17:
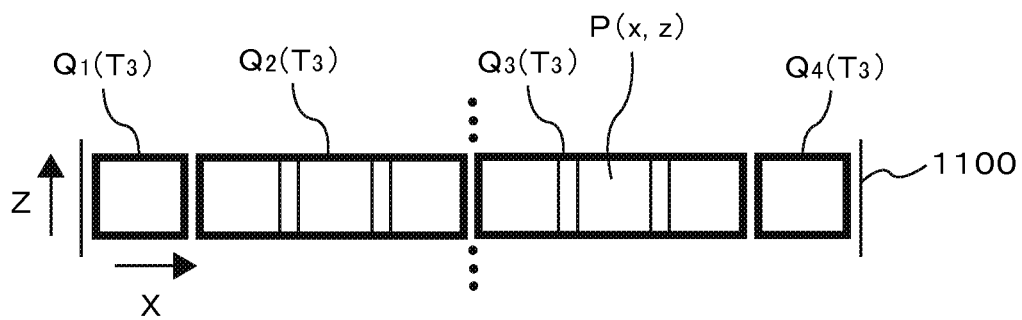

FIG. 17 is diagrams for describing another example of the pixel addition performed in each detector module 1100. Incidentally, the present example is the one that KX=8, and the image scanning mode conditions have been set as NX=3, Nz=1, MX=2, Mz=0. At that time, G=3 from Numerical Formula 1, and the respective addition positions $Q(T_1)$ to $Q(T_3)$ at the respective image scanning timings are respectively shown in (A) to (C) of FIG. 17. In addition, similarly to the case in FIG. 16, the respective addition positions are numbered in the form of $Q_1(T)$, $Q_2(T)$ ... in order from the left side. Although when the image scanning mode conditions NX=3, MX=2 of the present example are substituted into Numerical Formula 2, LX=4, a maximum value of the above-mentioned numbering becomes 4 in (C) of FIG. 17 in reality.

Figure 18:
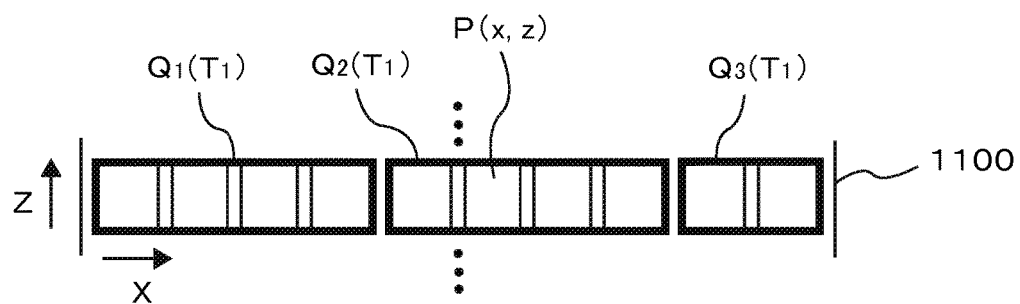
FIG. 18 is diagrams for describing a further another example of the pixel addition performed in each detector module, pertaining to the first embodiment.
Figure 18:
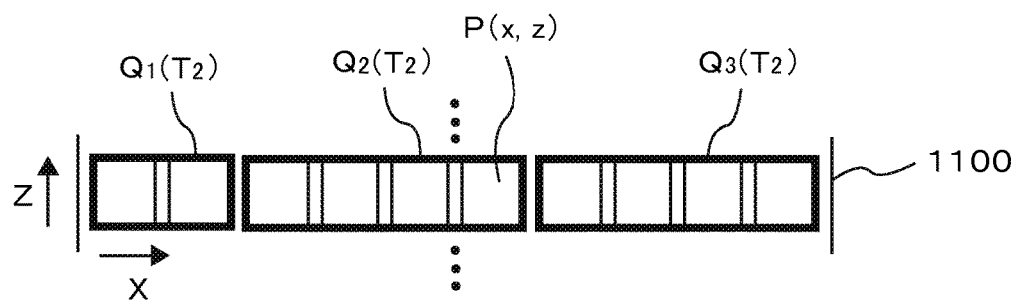

FIG. 18 is diagrams for describing a further another example of the pixel addition performed in each detector module 1100. Incidentally, the present example is the one that KX=10 and the image scanning mode conditions have been set as NX=4, Nz=1, MX=2, Mz=0. At that time, G=2 from Numerical Formula 1, and the respective addition positions $Q(T_1)$, $Q(T_2)$ at the respective image scanning timings are respectively shown in (A), (B) of FIG. 18. In addition, similarly to the case in FIG. 16, the respective addition positions are numbered in the form of $Q_1(T)$, $Q_2(T)$, ... in order from the left side. Although when the image scanning mode conditions NX=4, MX=2 of the present example are substituted into Numerical Formula 2, LX=3, the maximum value of the above-mentioned numbering becomes 3 in (C) of FIG. 18 in reality.

Figure 19:
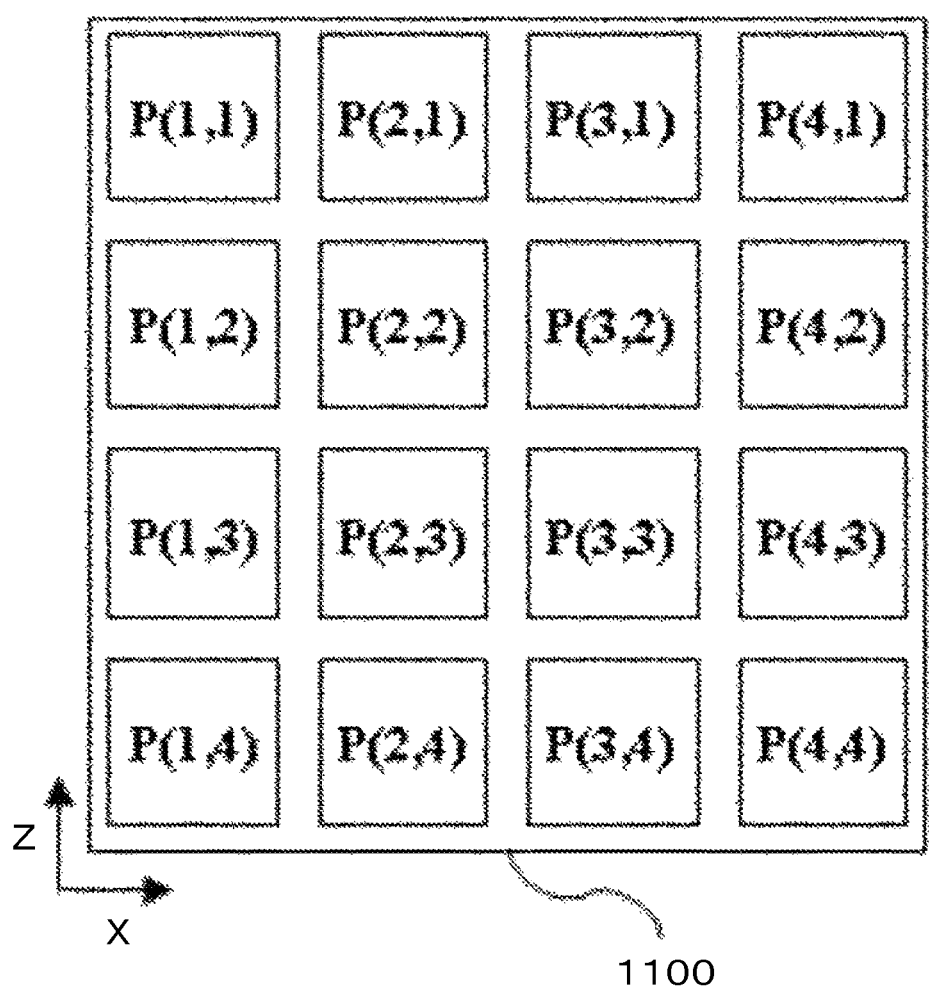
FIG. 19 is a diagram for describing one example of an array of detection pixels (X, z) in the detector module, pertaining to the first embodiment.
Figure 20:
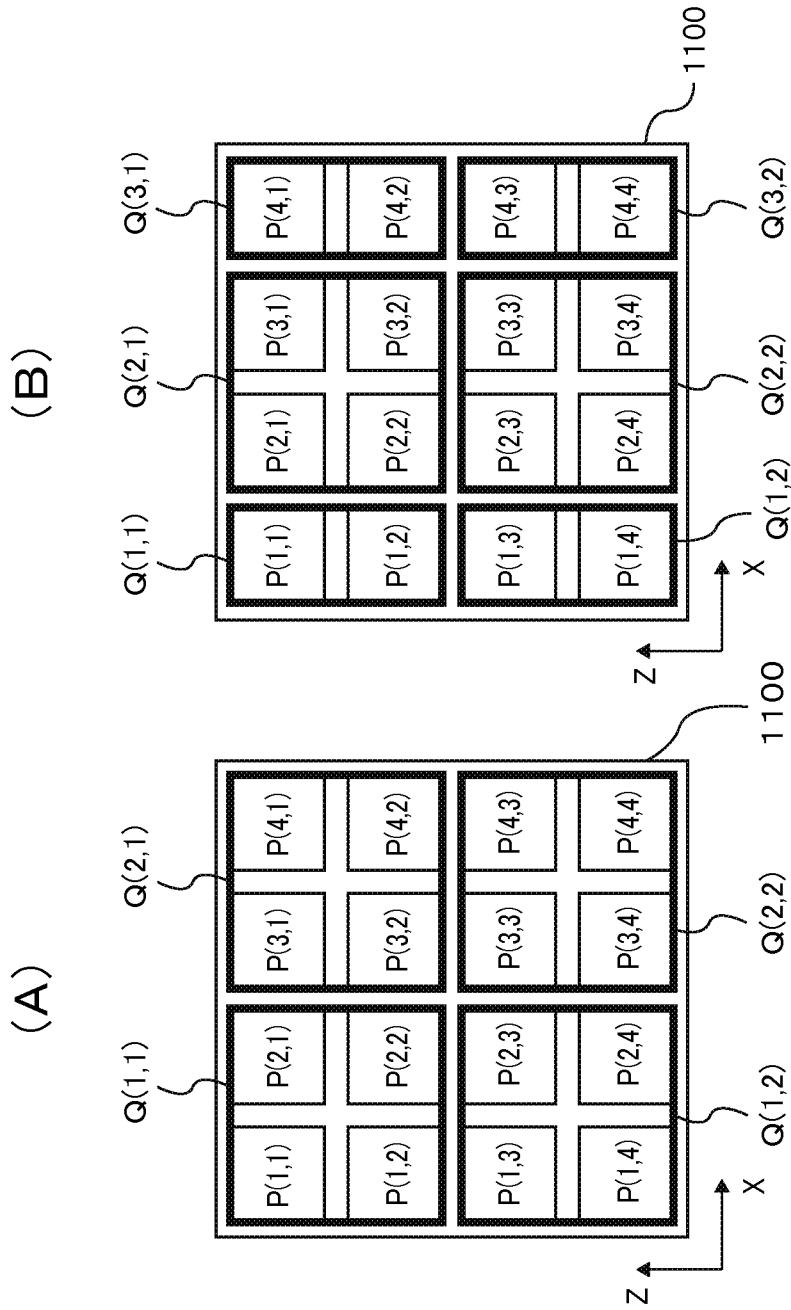
FIG. 20 is diagrams for describing an example of a pixel addition performed in the detector module in FIG. 19.

FIG. 19 is a diagram for describing one example of an array of the detection pixels P(X, z) in the detector module 1100 in the X-ray CT device of the present embodiment. In addition, FIG. 20 is diagrams for describing examples of the pixel addition performed in the detector module 1100 shown in FIG. 19. Further, FIG. 21 is a circuit diagram for describing a concrete example of the pixel addition circuit 1300 for implementing the pixel addition shown in FIG. 20.

In the following, details of a configuration of the pixel addition circuit 1300 of the present embodiment will be described by using FIGS. 19 to 21. The detector module 110 shown in FIG. 19 is the one that the array of the detection pixels P(X, z) has been shown in a case where KX=Kz=4, and the positions in the X and z directions of the detection pixels P (X, z) are respectively indicated by numerals 1 to 4. Incidentally, although, here, such a comparatively small numeral as KX=Kz=4 is set for simplicity, a further larger numeral is used in reality. For example, representative values of KX and Ky are KX=32 and Kz=128.

FIG. 20 is the one that the image scanning mode conditions have been set as NX=2, Nz=2, MX=1, Mz=0 for the detector module 1100 shown in FIG. 19. At that time, G=2 from Numerical Formula 1 and the respective addition positions Q(X, z) at the respective image scanning timings are shown in (A) and (B) of FIG. 20. However, similarly to the case of P(X, z), the positions in the X and z directions are respectively indicated by numerals 1 to 3. Incidentally, when NX=2, MX=1 are substituted into Numerical Formula 2, LX=3. In addition, when Nz=2 and Mz=0 are substituted into Numerical Formula 4, Lz=2. Accordingly, the added pixels amounting to the maximum LX×Lz=6 are generated in the present detector module 1100.

Figure 21:
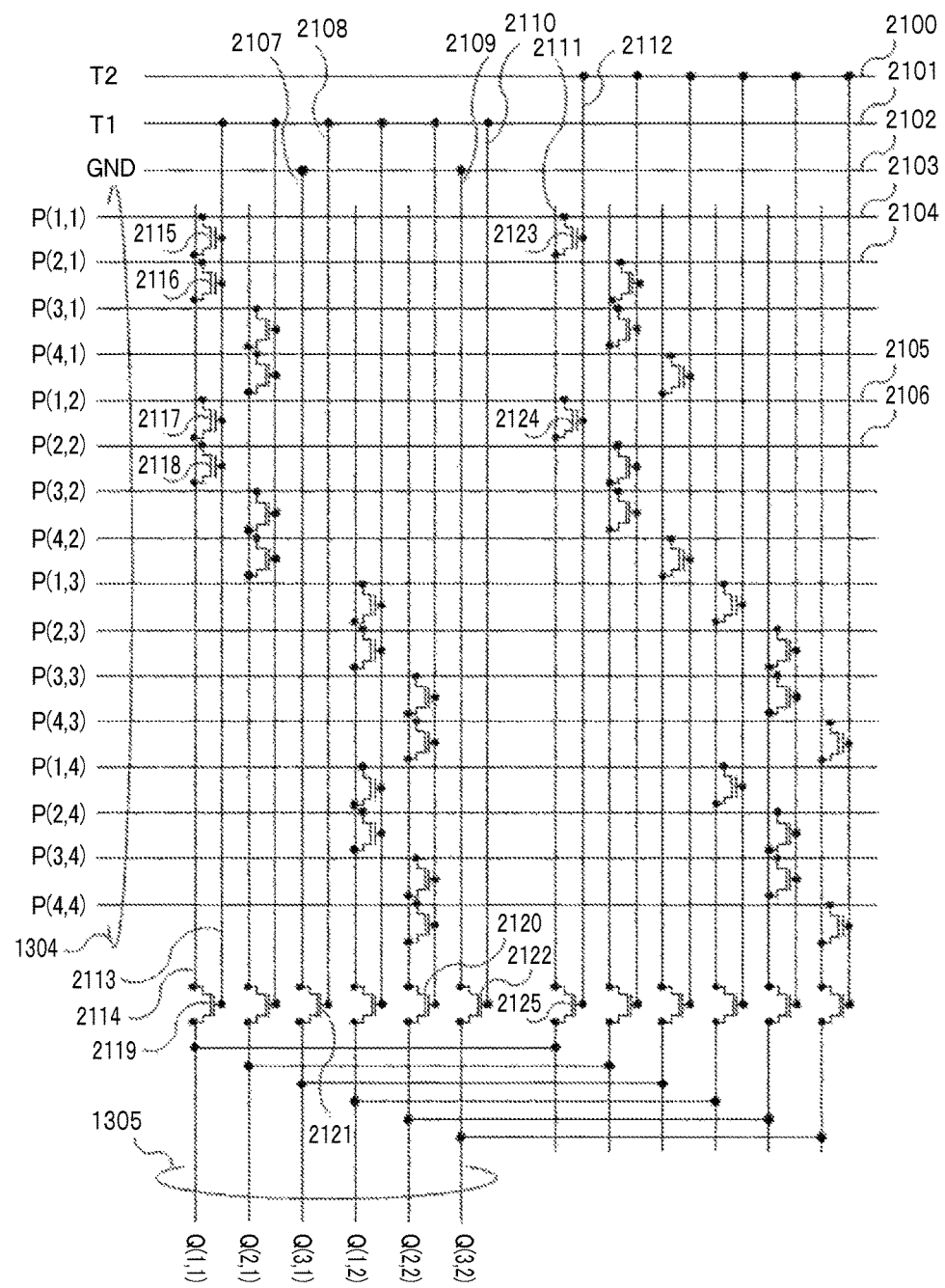
FIG. 21 is a diagram for describing an example of a pixel addition circuit for implementing the pixel addition shown in FIG. 20.

The pixel addition circuit 1300 shown in FIG. 21 is the one that a case where it is arranged at the first stage of the DAS chip 1203 shown in FIG. 13 has been supposed, and a signal input from the input signal line 1304 is a signal charge generated by the photodiode array 304. As shown in FIG. 19, 16 signals (=KX×Kz) in total from P(1,1) up to P(4,4) are output from the detector module 1100 and are input into the pixel addition circuit 1300 through the input signal lines 1304. On the other hand, as shown FIG. 20, after the pixel addition, 6 (=LX×Lz) signals in total from Q(1,1) up to Q(3,2) are generated and output from the pixel addition circuit 1300 through the output signal lines 1305.

In FIG. 21, switching between two image scanning timings T1 (corresponding to a pixel addition pattern in (A) of FIG. 20) and T2 (corresponding to a pixel addition pattern in (B) of FIG. 20) is implemented by alternating switching ON/OFF of switch voltages T1, T2 to be input into signal lines 2101 and 2100. For example, in a case where the switch voltage T1 to be input into the signal line 2101 has been turned ON and the switch voltage T2 to be input into the signal line 2100 has been turned OFF, the above-mentioned switch voltage T1 is applied to gate voltages of switches 2115, 2116, 2117, 2118 and 2119 via signal lines 2101 and 2113 to turn all of the above-mentioned switches to ON states. Thus, the image scanning timings T1 and T2 that are sampling timings of the sample hold circuit are utilized in switching of the pixel addition positions in the X-ray CT device of the present embodiment and thus switching of the image scanning timings synchronizes with that of the pixel addition positions.

At that time, signal charges generated in detection pixels P(1,1), P(2,1), P(1,2), P(2,2) flow into a signal line 2114 respectively through signals lines 2103, 2104, 2105, 2106 and switches 2115, 2116, 2117, 2118 and are added together. In addition, the above-mentioned addition signal is output as an added pixel signal Q(1,1) via a switch 2119. Incidentally, at that time, since the switch voltage T2 is OFF, switches 2123, 2124 and 2125 are all in OFF states. Therefore, it does not occur that another signal charge flows into the added pixel signal Q(1,1). All of 6 added pixel signals in total from Q(1,1) up to Q(3,2) are generated similarly. However, since no added pixel signals Q(3,1) and Q(3,2) are present at the image scanning timing T1 as shown in (A) of FIG. 20, a GND signal is output for them.

The above-mentioned GND signal is supplied via signal lines 2102, 2107 and 2109 and is output via switches 2121 and 2122. On the other hand, in a case where the switch voltage T1 to be input into the signal line 2101 has been turned OFF and the switch voltage T2 to be input into the signal line 2100 has been turned ON, the above-mentioned switch voltage T2 is applied to gate voltages of the switches 2123, 2124 and 2125 via the signal lines 2100 and 2112 and turns all of the above-mentioned switches to the ON states. At that time, the signal charges generated in the detection pixels P(1,1), P(2,1) flow into a signal line 2111 respectively via the signal lines 2103, 2105 and the switches 2123, 2124 and are added together. In addition, the above-mentioned addition signal is output as the added pixel signal Q(1,1) via the switch 2125. Incidentally, at that time, since the switch voltage T1 is turned OFF, the switches 2115, 2116, 2117, 2118 and 2119 are all in the OFF states. Therefore, it does not occur that another signal charge flows into the added pixel signal Q(1,1). All of the 6 added pixel signals in total from Q(1,1) up to Q(3,2) are generated similarly. The position of the added pixel can be switched by alternately switching ON/OFF of the switch voltages T1 and T2 as mentioned above.

Figure 22:
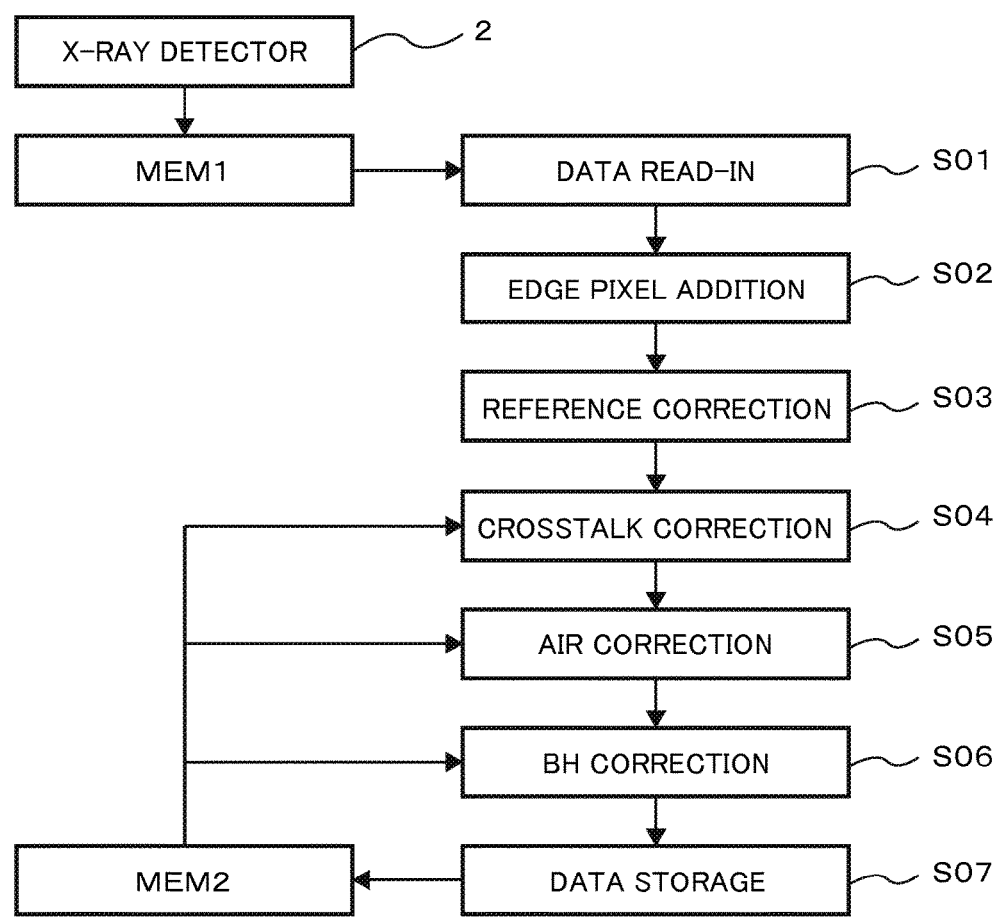
FIG. 22 is a flowchart for describing procedures of a preprocessing operation that has been described by using FIG. 1.

FIG. 22 is a flowchart for describing procedures of the preprocessing operation in the X-ray CT device of the present embodiment that has been described using FIG. 1. Incidentally, steps S01 to S07 shown in FIG. 22 are performed by operations of the computer CPU that functions as the signal processing unit shown in FIG. 1. Image scanning data that has been output from the X-ray detector 2 and then transmitted from the rotational tomography system to the static system is stored into the memory MEM1. Simultaneously with storage of the image scanning data into the memory MEM1, the computer CPU, first, reads in the above-mentioned image scanning data from MEM1 (step S01), and performs the operation for edge pixel addition (step S02). Here, contents of the edge pixel addition will be described by using FIGS. 23 and 24.

Figure 23:
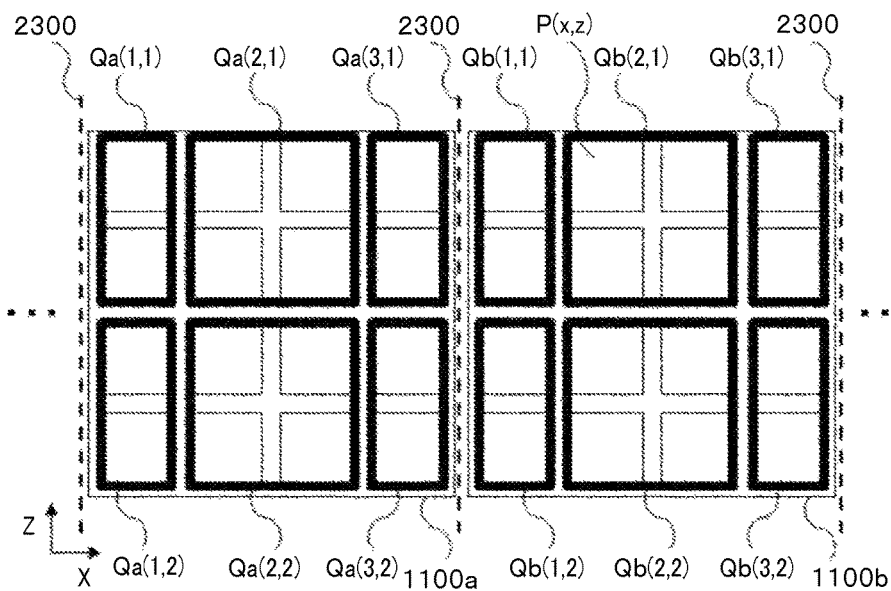
FIG. 23 is a diagram for describing one example of operation details for an edge pixel addition, pertaining to the first embodiment.

FIG. 23 is a schematic diagram for describing one example of the contents of the operation for the edge pixel addition in the X-ray CT device of the present embodiment. Incidentally, some detector modules 1100a and 1100b in a case where the detector modules 1100 shown in FIG. 19 have been arrayed in the X direction to configure the X-ray detector 2 are shown in FIG. 23. In addition, the added pixel position Q(X, z) (the image scanning mode conditions: NX=2, Nz=2, MX=1, Mz=0) shown in (B) of FIG. 20 is shown in FIG. 23. As already described, the added pixel signals are individually converted into the digital signals per detector module 1000 and are output. At that time, in the added pixels in the vicinity of a module boundary 2300, outputs of the added pixels not meeting the set number of added ones NX are generated. For example, in FIG. 23, since the added pixel signals that are output from added pixel positions Qa(3,1) and Qb(1,1) do not respectively meet the number of added ones NX in the X direction, it is necessary to form one added pixel signal by numerically adding both of the digitally output signals. Digital signals that are output from added pixel positions Qa(3,2) and Qb(1,2) are also added similarly. In the following, such an addition operation will be called the edge pixel addition. The edge pixel addition is performed on all of added pixel outputs in the vicinity of the module boundary 2300 that do not meet the numbers of added ones NX, Nz.

Figure 24:
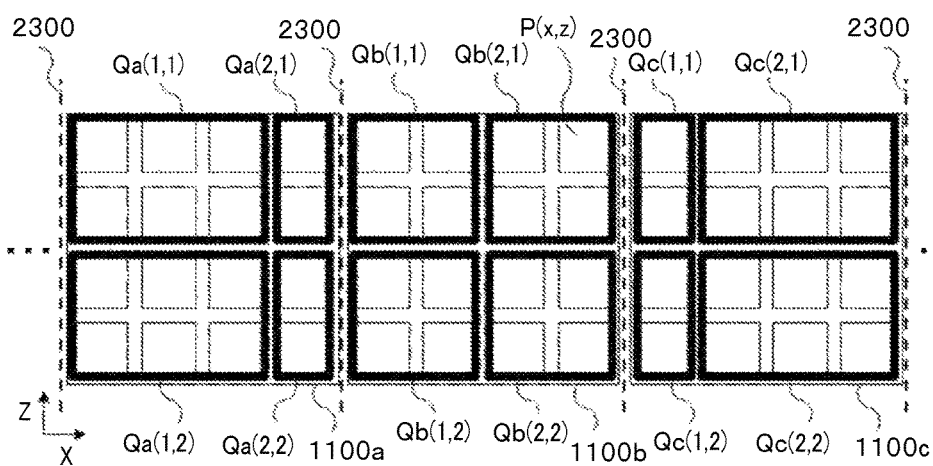
FIG. 24 is a diagram for describing another example of the operation details for the edge pixel addition, pertaining to the first embodiment.

FIG. 24 is a diagram for describing another example of the contents of the operation for the edge pixel addition. Incidentally, some detector modules 1100a, 1100b and 1100c in a case where the detector modules 1100 shown in FIG. 19 have been arrayed in the X direction to configure the X-ray detector 2 are shown in FIG. 24. In addition, in FIG. 24, there is shown the added pixel position Q(X, z) at one image scanning timing in a case where the image scanning mode conditions have been set as NX=3, Nz=2, MX=1, Mz=0. At that time, G=3 from Numerical Formula 1 and there exist 3 image scanning timings. In the present example, the edge pixel addition is performed, for example, on the added pixel positions Qa(2,1) and Qb(1,1) in the vicinity of the module boundary 2300. The edge pixel addition is also performed on Qb(2,1) and Qc(1,1), Qa(2,2) and Qb(1,2), Qb(2,2) and Qc(1,2) and so forth similarly. Incidentally, in the case of the present example, respectively different added pixel positions are set in the detector modules 1100a, 1100b and 1100c such that the number of added ones NX in the X direction always becomes 3 that is the set value in the edge pixel addition. Such changing of the added pixel position per detector module is implemented by setting time phases of the above-mentioned 3 image scanning timings of G=3 by shifting per detector module. In the foregoing, the contents of the operation for the edge pixel addition shown in step S02 in FIG. 22 have been described.

Next, returning to FIG. 22, succeeding steps will be described. Incidentally, although all steps that will be described hereinbelow are different from the conventional ones in the point that they are performed on added pixels, a well-known method is utilized in the contents of its operation. When the edge pixel addition in step S02 is terminated, next, an operation for reference correction is performed (step S03). The reference correction is a well-known operation performed in order to standardize the output of the above-mentioned image scanning data and is calculated by the following Formula 5.

$$Q_g'(X,z)=Q_g(X,z)/Q_{go} \quad (g=1,2, \ldots, G, X=1,2, \ldots VX, z=1,2, \ldots Vz)$$ (Formula 5)

wherein it is assumed that g is an image scanning timing, VX, Vz are respectively the numbers of added pixels in the X and z directions generated after the edge pixel addition, and $Q_g(X, z)$ is a signal value of the added pixel.

In addition, $Q_{go}$ is an average value of air data (corresponding to data not transmitting through the object 10) measured in the added pixels in the vicinity of the both ends in the X direction of the X-ray detector 2. Even in a case where the intensity of the X-ray output from the X-ray tube 1 has fluctuated during image scanning due to lack of precision of the device, the precision of succeeding CT reconstruction operations can be improved by removing a change in signal amount caused by the above-mentioned fluctuation by the above-mentioned reference correction. When the reference correction in step S03 is terminated, next, crosstalk correction is performed (step S04).

The crosstalk correction is an operation for recovering the spatial resolution that has been lowered caused by crosstalk by removing crosstalk signals that flow in from adjacent detection pixels by calculation, and various operation methods have been proposed so far. For example, as one of the simplest well-known operation methods, there is a method shown in Formula 6.

$$Q_g''(X,z)=Q_g'(X,z)-Q_g'(X-1,z) \times a_g(X,z)-Q_g'(X+1,z) \times b_g(X,z)-Q_g'(X,z+1) \times c_g(X,z)-Q_g'(X,z-1) \times d_g(X,z)$$
$$(g=1,2,\ldots,G, X=1,2,\ldots VX, z=1,2,\ldots Vz)$$ (Formula 6)

wherein $a_g(X, z)$, $b_g(X, z)$, $c_g(X, z)$ and $d_g(X, z)$ are ratios of signals to be mixed into $Q_g(X, z)$ from adjacent added pixels $Q_g(X-1, z)$, $Q_g(X+1,z)$, $Q_g(X, z+1)$ and $Q_g(X, z-1)$ for the added pixel $Q_g(X, z)$ and hereinafter will be called crosstalk ratios.

Values of the crosstalk ratios that have been derived in advance on the basis of well-known experiments, well-known simulations and so forth are tabulated and are recorded in the memory MEM2. The above-mentioned tabulated values are read out from the memory MEM2 upon the crosstalk correction to be utilized in the operation by the above-mentioned Numerical Formula 6.

Figure 25:
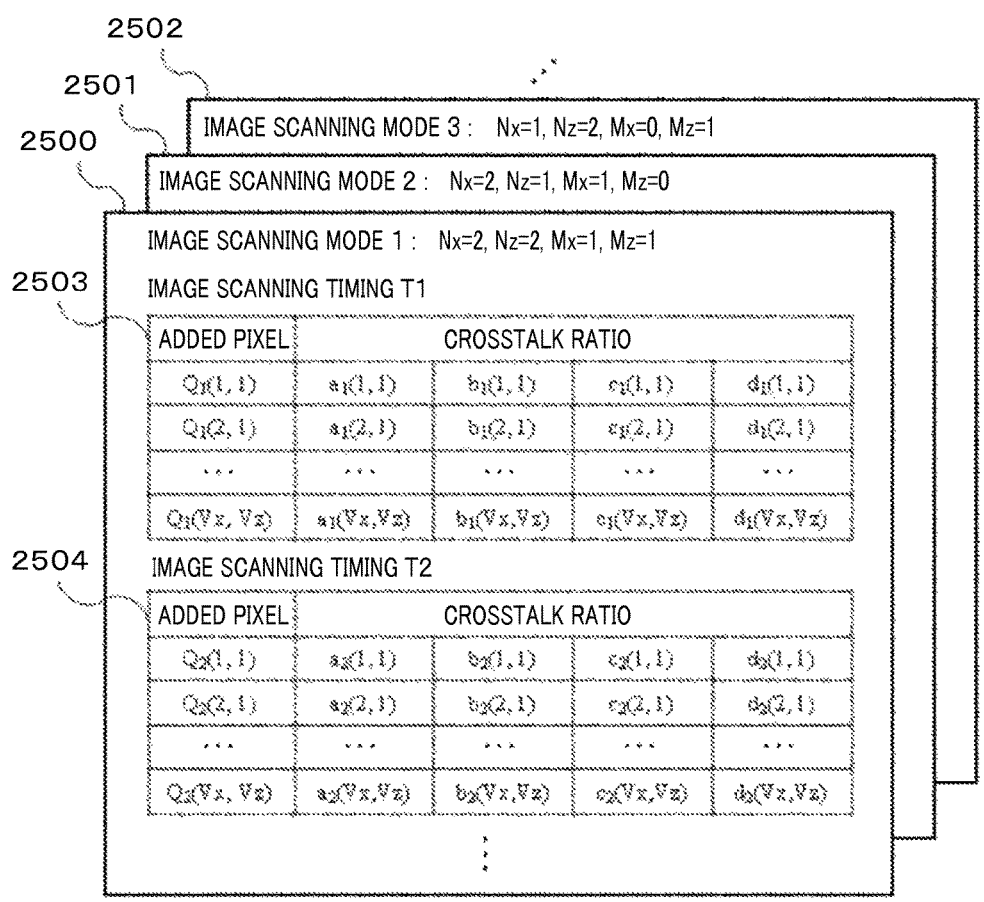
FIG. 25 is a diagram for describing a configuration of a crosstalk ratio table stored in a memory MEM, pertaining to the first embodiment.

FIG. 25 is a diagram for describing one configuration of a crosstalk ratio table stored in the memory MEM2 in the X-ray CT device of the present embodiment. It is necessary to obtain in advance the values of the crosstalk ratios for all of the added pixels to be generated in various image scanning modes. Therefore, in the X-ray CT device of the present embodiment, the tables for the crosstalk ratios are prepared for all settable image scanning modes in the form of a table 2500 for an image scanning mode 1, a table 2501 for an image scanning mode 2, a table 2502 for an image scanning mode 3, . . . . In addition, in each of the image scanning modes, tables are prepared for all of G image scanning timings in total that the image scanning mode has in the form of a table 2503 for the image scanning timing T1, a table 2504 for the image scanning timing T2, . . . .

Next, returning again to FIG. 22, steps succeeding to the crosstalk correction will be described. When the crosstalk correction (step S04) is terminated, next, air correction (step S05) and BH (Beam Hardening) correction (step S06) are performed. In calculations of the air correction and the BH correction, such well-known formulae as those respectively indicated by Formula 7 and Formula 8 are used.

$$R_g(X,z) = -\log(Q_g''(X,z)/A_g(X,z)) \quad (g=1,2, \ldots G, \; X=1,2, \ldots VX, \; z=1,2, \ldots Vz) \quad \text{(Formula 7)}$$

$$R'_g(X,z) = \alpha_g(X,z) \times R_g(X,z)^2 + \beta_g(X,z) \times R_g(X,z) \quad (g=1,2, \ldots G, \; X=1,2, \ldots VX, \; z=1,2, \ldots Vz) \quad \text{(Formula 8)}$$

wherein $A_g(X, z)$ is well-known air data that has been measured in advance for the added pixel $Q_g(X, z)$.

The air data is the one that, after the edge pixel addition (step S02), the reference correction (step S03), the crosstalk correction (step S04) that have already been described by using FIG. 22 have been performed on the image scanning data that has been captured without arranging the object 10 and the bed top plate 4, these have been added in plural and averaged. In addition, $\alpha_g(X, z)$ and $\beta_g(X, z)$ are well-known BH correction coefficients that have been measured in advance for the added pixel $Q_g(X, z)$. Since a well-known method such as that, for example, described in Japanese Examined Patent Publication Sho61-54412 (Patent Literature) can be utilized for derivation of the BH correction coefficients, description thereof is omitted hear. For the air data $A_g(X, z)$ and the BH correction coefficients $\alpha_g(X, z)$ and $\beta_g(X, z)$, values that have been obtained in advance are tabulated and recorded in the memory MEM2. The above-mentioned table values are respectively read out from the memory MEM2 upon the air correction and the BH correction and are used in operations by the above-mentioned Numerical Formula 7 and Numerical Formula 8.

Figure 26:
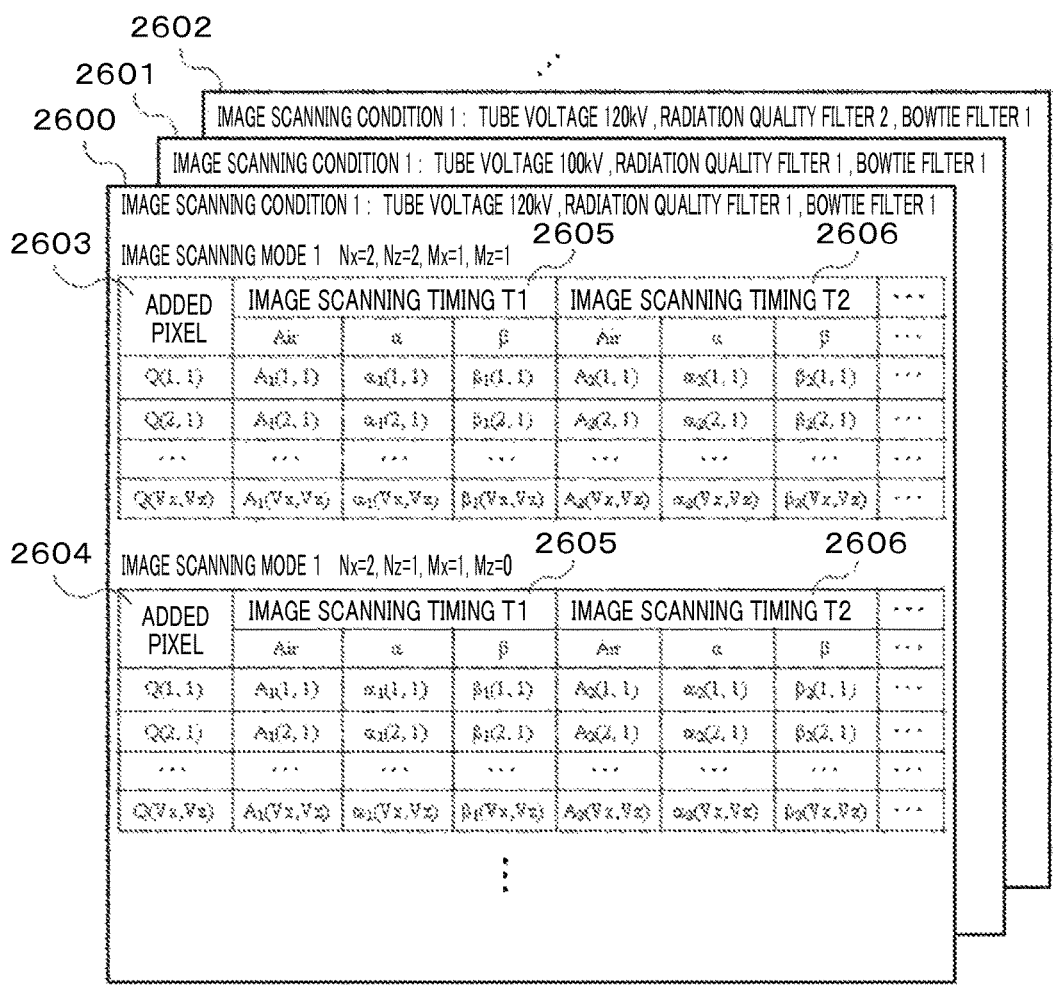
FIG. 26 is a diagram for describing a configuration of an air data and BH correction coefficient table stored in the memory MEM, pertaining to the first embodiment.

FIG. 26 is a diagram for describing one concrete configuration of tables for the air data and the BH correction coefficients stored in the memory MEM2 in the X-ray CT device of the present embodiment. It is necessary to obtain in advance the values of the air data and the BH correction coefficients for all of added pixels to be generated under various image scanning conditions, for example, settable combined conditions and so forth of the tube voltage of the X-ray tube 1, the kind of the radiation quality filter 7, the kind of the bowtie filter 8. Therefore, the tables for the air data and the BH correction coefficients are prepared for all of settable image scanning conditions in the form of a table 2600 for an image scanning condition 1, a table 2601 for an image scanning condition 2, a table 2602 for an image scanning condition 3, . . . . In addition, in each of the image scanning conditions, tables are prepared for all of settable image scanning modes in the form of a table 2603 for the image scanning mode 1, a table 2604 for the image scanning mode 2, . . . . Further, in each of the image scanning modes, tables are prepared for all of the G image scanning timings in total that the image scanning mode has in the form of a table 2605 for the image scanning timing T1, a table for the image scanning timing T2, . . . .

Returning again to FIG. 22, the data after BH corrected (step S06) is finally stored into MEM2 (step S07). Incidentally, processes of the preprocessing operation from the above-mentioned steps S01 to S07 are repetitively performed every time the image scanning data output from the X-ray detector 2 is stored into the memory MEM1 during image scanning and the preprocessing operation is terminated at the time point that the operation has been terminated for all pieces of the image scanning data.

Figure 27:
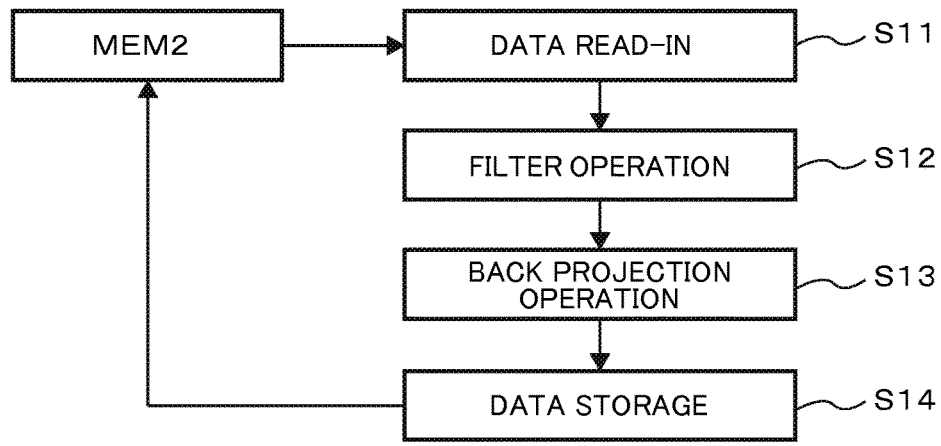
FIG. 27 is flowcharts for describing procedures of a reconstruction operation for the CT image that has been described using FIG. 1.
Figure 27:
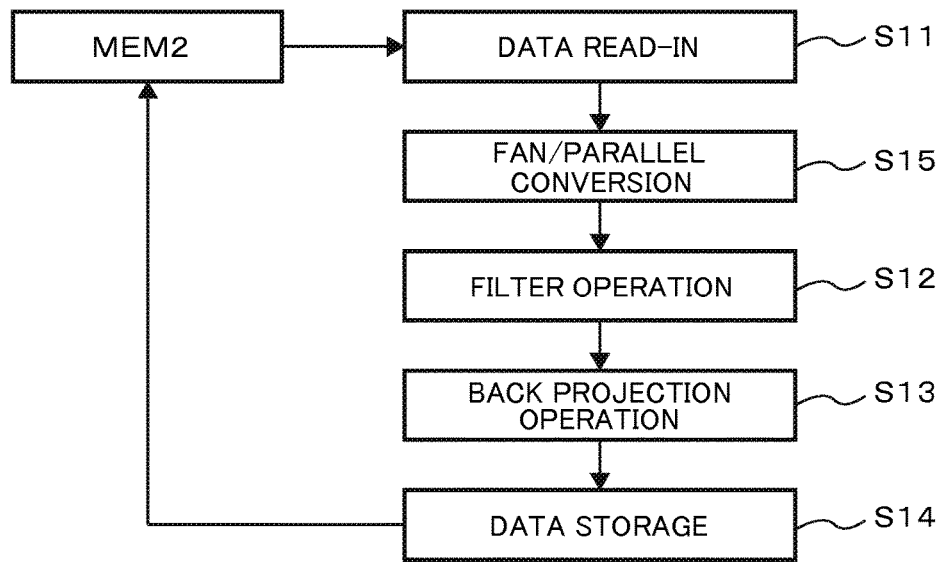

(A) of FIG. 27 is a flowchart for describing procedures of one example of the reconstruction operation for the CT image that has been described by using FIG. 1 in the X-ray CT device of the present embodiment. Incidentally, steps S11 to S14 shown in (A) of FIG. 27 are performed by operations of the computer CPU. In addition, although in relation to the reconstruction algorithm, various systems have been proposed and publicly known so far, in the following, the procedures of the reconstruction operation will be described, targeting the most common Feldkamp algorithm (Known Literature 1: J. Opt. Soc. Am. A, vol. 1, pp. 612-619, June 1984). However, it is not limited to this reconstruction operation as described later.

Simultaneously with storage of the image scanning data the preprocessing operation described in FIG. 22 on which has been terminated into the MRM2, the computer CPU, first, reads in the above-mentioned image scanning data from MEM2 (step S11) and performs a filter operation (step S12). Although since a method for the filter operation is stated in the above-mentioned Known Literature 1, detailed description thereof is omitted here, simply speaking, it is an operation for convoluting a digital filter that is called a reconstruction filter relative to the image scanning data in the X direction. In the present X-ray CT device, the filter operation is performed on the data after the pixels have been added. In this occasion, although the positions in the X direction and the z direction of the added pixels are different at every image scanning timing, the filter operation is performed by the same method as the conventional one regardless of the above-mentioned positional change. Next, a back projection operation is performed by using the image scanning data after the filter operation has been terminated (step S13). Although the method stated in the above-mentioned Known Literature 1 is basically utilized also in the back projection operation similarly to the filter operation, since the X-ray CT device of the present embodiment is characterized in a creation method for back projection data to be used in the back projection operation, in the following, details of the back projection operation in the X-ray CT device of the present embodiment will be described by using FIG. 28 and FIG. 29.

Figure 28:
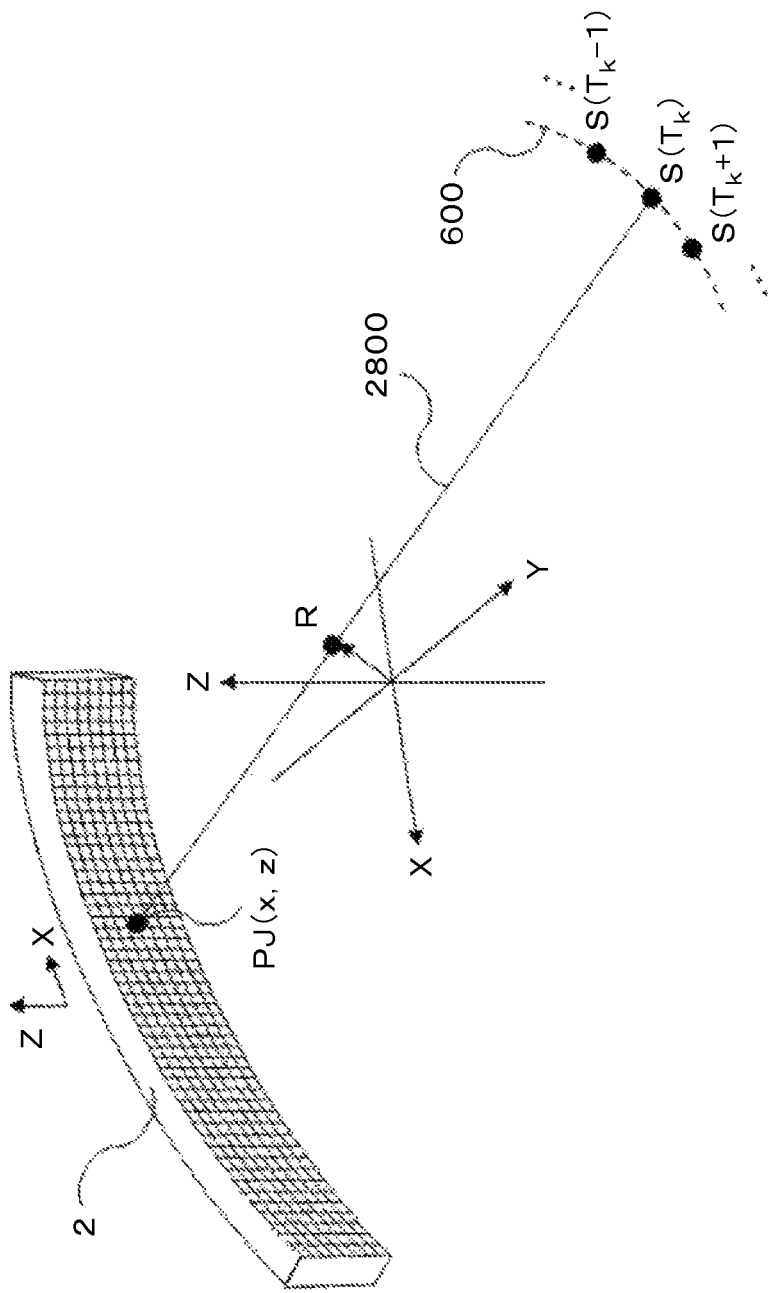
FIG. 28 is a diagram for describing an operation method for a back projection operation, pertaining to the first embodiment.

FIG. 28 is a diagram for describing an operation method for the back projection operation. The CT image is generated by calculating reconstruction data for all of reconstruction points R on XYZ coordinates that constructs the above-mentioned CT image. In order to calculate the reconstruction data at the reconstruction points R, first, the position (X, z) (hereinafter, referred to as a projection position) where a straight line 2800 that connects together an X-ray generation point S(Tk) and the reconstruction point R at the image scanning timing $T_k$ intersects with the X-ray detector 2 is calculated, and image scanning data $PJ_k(X, z)$ (hereinafter, referred to as back projection data) at the above-mentioned projection position is obtained by an interpolation operation for image scanning data that will be described later (however, the image scanning data called here is the image scanning data after the filter operation shown in step S12 in (A) of FIG. 27). The above-mentioned back projection data is calculated as $PJ_k(X, z)$, $PJ_{k+1}(X, z)$, . . . for all of the X-ray generation point positions $S(T_k)$, $S(T_{k+1})$, . . . in a whole circumference direction surrounding the reconstruction point R, and the reconstruction data at the reconstruction point R can be calculated by adding them. Incidentally, the above-mentioned calculation for adding the back projection data is called the back projection operation.

Figure 29:
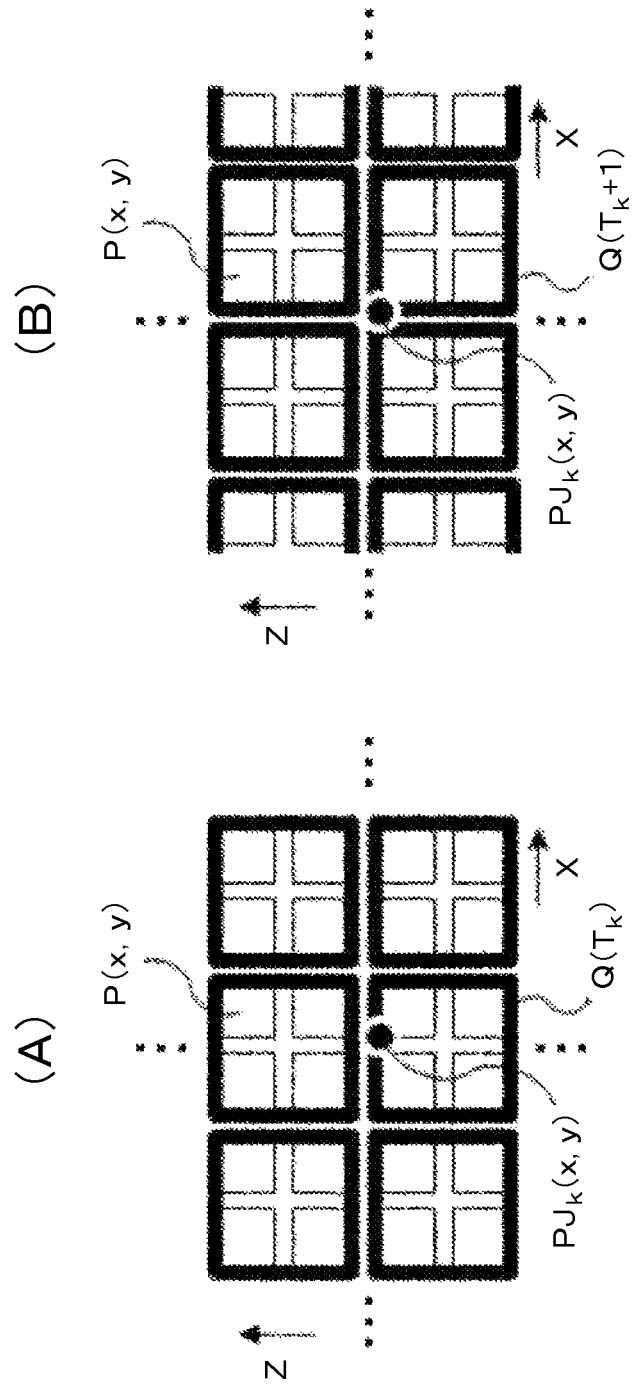
FIG. 29 is diagrams for describing a calculation method for back projection data based on an interpolation operation, pertaining to the first embodiment.

FIG. 29 is diagrams for describing a calculation method for the back projection data on the basis of the interpolation operation. Since the projection positions (X, z) of the back projection data can be present variously for the array of the added pixel positions Q on the X-ray detector 2, the value of the back projection data $PJ_k(X, z)$ is calculated by interpolating the image scanning data that has been measured in the added pixel in the periphery of the projection position (X, z). At that time, since the position of the added pixel is changed to $G(T_k)$ (see (A) of FIG. 29), $G(T_{k+1})$ (see (B) of FIG. 29) and so forth at every image scanning timing, interpolation data is created, taking the positional change of each added pixel into account. Incidentally, well-known methods such as linear interpolation, Lagrange's interpolation and so forth are utilized for the above-mentioned interpolation operation. Returning again to (A) of FIG. 27, the CT image created by the back projection operation (step S13) is finally stored into MEM2 (step S14), and the reconstruction operation is terminated.

As described above, in the X-ray CT device pertaining to the present embodiment, the detection pixels of the X-ray detector are pixel-added and the above-mentioned pixel addition position is changed at every image scanning timing. At that time, the sampling interval of the data is reduced by changing the above-mentioned pixel addition position with a moving distance that is smaller than the size of the added pixel and thereby the Nyquist frequency can be improved. As a result, since the amount of the high spatial resolution information included in the object that is lost by aliasing can be reduced, the spatial resolution of the CT image can be improved.

In addition, in the X-ray detector 2 shown in the present embodiment, although the size in the X direction and the z direction of the detection pixel has been defined as 0.5 [mm], this is the size that is about one-half of the same size used in a general medical X-ray CT device. In this case, although the doze of X-rays to be input into one detection pixel is reduced to one-quarter of the general one and the S/N of the CT image to be measured is reduced, since the four detection pixels are added by adopting the image scanning mode conditions NX=2, Nz=2, MX=1, Mz=1 such as those, for example, shown in FIG. 5, the reduction in the above-mentioned S/N can be prevented. That is, there is such an advantage that, without reducing the S/N of the CT image, the spatial resolution thereof can be improved.

Further, when the size of the detection pixel is halved in the X direction and the y direction as mentioned above, the total number of the detection pixels increases fourfold, and therefore when circuits for reading out the signal are provided in parallel for all of the detection pixels, such a problem occurs that the number of the above-mentioned parallel circuits and the number of pieces of data to be output increase also fourfold. Such an increase in number of parallel circuits not only causes increases in cost of the X-ray detector and the power consumption amount but also causes an increase in amount of heat generation from the circuit to induce a malfunction. Further, since the amount of information to be transmitted from the rotational tomography system to the static system via the optical slip ring increases fourfold with increasing the number of pieces of the above-mentioned output data fourfold, the malfunction such as a transmission error and so forth becomes liable to occur. However, in the X-ray CT device shown in the present embodiment, the above-mentioned high spatial resolution measurement can be implemented almost never increasing the number of the above-mentioned parallel circuits and the number of pieces of the output data, by providing the pixel addition circuit 1300.

For example, in the X-ray CT device shown in the present embodiment, since the numbers of detection pixels in the X direction and y direction of the detector module 1100 have been respectively defined as KX=32, Kz=128, one detector module 1100 has 32×128=4096 detection pixels in total. On the other hand, in the general detector module having the detection pixels of the above-mentioned general sizes, the total number of the detection pixels amounts to 1024 (KX=16, Kz=64, KX×Kz=1024) that is one-quarter of that of the above-mentioned example. However, in the X-ray CT device shown in the present embodiment, it is possible to suppress the total number of the above-mentioned parallel circuits to 1105 (LX=17, Lz=65, LX×Lz=1105 from Numeral Formula 2) by providing the above-mentioned pixel addition circuit 1300. That is, the signal read-out circuit can be configured by increasing the number of parallel circuits only about by 8% relative to 1024 that is the total number of the parallel circuits that the above-mentioned general detector module has. Therefore, there can be implemented the X-ray CT device that enables high spatial resolution measurement, without increasing the cost of the X-ray detector and the power consumption amount that have been the problems incidental to the increase in number of the parallel circuits and further almost never inducing occurrence of the malfunction and so forth incidental to the increase in heat generation amount.

Although one embodiment of the X-ray CT device pertaining to the present invention has been shown as mentioned above, the present invention is not limited to the present embodiment, and it goes without saying that it can be modified in a variety of ways within a range not deviating from the gist thereof. In addition, the above-described embodiment has been described in detail for better understanding of the present invention, and it is not necessarily limited to those provided with all configurations described.

For example, although an example that the Feldkamp algorithm is utilized as the reconstruction algorithm has been shown in the example of the present embodiment, other well-known algorithms may be utilized. At that time, in many reconstruction algorithms, after the image scanning data to be measured in a fan beam type coordinate system has been transformed into that of a parallel beam type coordinate system, reconstruction by the filter operation and the back projection is performed. Although in the above-mentioned coordinate transformation (fan/parallel transformation), the interpolation operation of fan beam data is performed in order to obtain desired parallel beam data, when performing the above-described interpolation operation, the parallel beam data corresponding to the change of the added pixel position can be calculated by a method that is the same as the interpolation operation method shown in FIG. 29, by replacing $PJ_k(X, y)$ shown in FIG. 29 with the desired parallel beam data and the added pixel $G(T_k)$ with the fan beam data. The reconstruction flow in this case is configured so as to perform the filter operation after the image scanning data has been read in (step S11) and after fan/parallel transformation (step S15) has been performed as shown in (B) of FIG. 27.

Further, although there has been described a case where each configuration, function, processing unit and so forth of the above-mentioned embodiment are implemented by software by creating a program that implements some or all of them, it goes without saying that some or all of them may be implemented by hardware by, for example, designing them by an integrated circuit and so forth.

The X-ray CT device of the present invention can improve the spatial resolution without reducing the S/N of the X-ray CT image to be measured. Thereby, for example, in the industrial CT, measurement of the fine structure of the object becomes possible without increasing the output of the X-ray from the X-ray generator in order to improve the S/N and extension of the service life and low power consumption of the X-ray generator are implemented, and the measurement precision for the object can be improved. In addition, for example, in the medical CT, it is remarkably useful because measurement of a finer structure such as that of the blood vessel and so forth becomes possible without increasing exposure of the object for the purpose of improving the S/N and the diagnosability can be improved.

REFERENCE SIGNS LIST

1 . . . X-ray tube
2 . . . X-ray detector
3 . . . rotating plate
4 . . . bed top plate
5 . . . gantry
6 . . . opening
7 . . . radiation quality filter
8 . . . bowtie filter
9 . . . collimator
10 . . . object
CPU . . . computer
MEM1 . . . memory
MEM2 . . . memory
CTL . . . image scanning controller
CSL . . . console
MNT . . . monitor
300 . . . scattering ray removing collimator
301 . . . scintillator block
302 . . . light reflector
303 . . . scintillator array
304 . . . photodiode array
305 . . . photodiode element
306 . . . output signal line
307 . . . slit
900 . . . detector central area
901 . . . detector peripheral area
1100 . . . detector module
1200 . . . substrate
1201 . . . substrate
1202 . . . flexible wiring
1203 . . . DAS (Data Acquisition System) chip
1300 . . . pixel addition circuit
1301 . . . CA (Charge Amplifier) circuit array
1302 . . . SH (Sample Hold) circuit array
1303 . . . ADC (Analog-to-Digital Converter) circuit array
1304 . . . input signal line
1305 . . . output signal line

The invention claimed is:

1. An X-ray CT device that generates a CT image of an object, comprising:
an X-ray tube;
an X-ray detector that detects an X-ray image irradiated from the X-ray tube;
a rotating plate that rotates the X-ray tube and the X-ray detector around an axis of rotation; and
a DAS (Data Acquisition System) chip that reads out a signal detected by the X-ray detector at a predetermined image scanning timing and a signal processor that processes a signal that has been output from the DAS chip to generate the CT image of the object,
wherein the DAS chip adds and outputs signals detected by Nx detection pixels that are adjacent in an X direction and/or Nz detection pixels that are adjacent in a z direction in a plurality of detection pixels configured in a matrix on an X-ray input plane of the X-ray detector, and performs changing of an addition position of the detection pixel where an addition is performed in synchronization with the image scanning timing,
wherein the X-ray detector is provided with a plurality of small regions that have been set in advance in a detection region and arranged in an X direction,
wherein values of the Nx and Nz can be individually set for the plurality of small regions in accordance with a purpose of imaging scanning,
wherein the Nx and Nz are integers of 1 or more and either one of the Nx and Nz is 2 or more,
wherein the signal processor performs a correction operation for reducing a reduction in spatial resolution caused by crosstalk, by using an amount of the crosstalk between an added pixel concerned and an added pixel that is adjacent to the added pixel concerned for all added pixels that are formed in a frame cycle of changing of the addition position, wherein a large pixel unit formed by adding the detection pixels is referred to as the added pixel,
wherein the signal processor performs a back projection operation to produce interpolation data by executing interpolation using data obtained in a plurality of different adding positions to reduce a sampling interval and to improve a Nyquist frequency, the produced interpolation data including a smaller sampling interval than adding position, and
wherein the signal processor generates the CT image, by using calibration data needed when generating the CT image for all added pixels formed in a frame cycle of changing of the addition position.

2. The X-ray CT device according to claim 1, wherein the DAS chip cyclically changes the addition position of the detection pixel where the addition is performed.

3. The X-ray CT device according to claim 1, further comprising:
a setting screen that designates the Nx and Nz.

4. The X-ray CT device according to claim 1, further comprising:
a display that is to be connected to the signal processor, wherein the setting screen is configured by a display screen of the display.

5. The X-ray CT device according to claim 1, wherein the plurality of small regions are a detector central area, and two detector peripheral areas interposing the detector central area.

6. The X-ray CT device according to claim 1, wherein the DAS chip includes a pixel addition circuit that adds an output signal from the X-ray detector, a signal detected by the detection pixels, a sample hold circuit that samples the signal detected by the detection pixel at a predetermined timing, and an ADC circuit that converts the signal detected by the detection pixel into a digital signal.

7. The X-ray CT device according to claim 6, wherein the image scanning timing is the predetermined timing of the sample hold circuit.

8. The X-ray CT device according to claim 7, wherein the pixel addition circuit is disposed at a front stage of the sample hold circuit, at a rear stage of the sample hold circuit, or at a rear stage of the ADC circuit.

9. The X-ray CT device according to claim 1, wherein the DAS chip sets minimum units of position change amounts in the x direction and the z direction in which the addition position is changed respectively as Mx and Mz, wherein, Mx is an integer of 0≤Mx<Nx, and Mz is an integer of 0≤Mz<Nz, sets either one of the Mx and Mz to 2 or more, or value(s) of the Mx and/or Mz can be designated from within 2 or more kinds of different choices.

10. The X-ray CT device according to claim 9, wherein the X-ray detector is configured by arraying a plurality of small X-ray detectors, Kx is a number of the detection pixels in the x direction, and Lx is a maximum value of a number of signals outputted in the X direction, wherein the DAS chip parallel-processes Lx ones to allocate in the respective x directions of the small X-ray detectors by one of:

in a case that Nx is 2 or more and Mx is 1 or more, Kx=Nx×Jx+Ix, Ix is an integer that meets 0≤Ix<Nx, Lx=Jx+1 in a case where Ix=0, or Ix=1, or Ix=Mx and Nx is a multiple of Mx, or in a case other than the above Lx=Jx+2.

11. The X-ray CT device according to claim 9, wherein the X-ray detector is configured by arraying a plurality of small X-ray detectors, Kz is a number of the detection pixels in the z direction, and Lz is a maximum value of a number of signals outputted in the z direction, wherein the DAS chip parallel-processes Lz ones to allocate in the respective z directions of the small X-ray detectors by one of:

in a case that Nz is 2 or more and Mz is 1 or more, Kz=Nz×Jz+Iz, Iz is an integer that meets 0≤Iz<Nz, Lz=Jz+1 in a case where Iz=0, or Iz=1, or Iz=Mz and Nz is a multiple of Mz, or in a case other than the above, Lz=Jz+2.

12. The X-ray CT device according to claim 1, further comprising:

a memory that stores the crosstalk amount that has been calculated in advance.

13. The X-ray CT device according to claim 1, further comprising: a memory that stores the calibration data that has been calculated in advance.

* * * * *